ard tumor DNA damage or cell death. $^{18}O$ transmutation to $^{18}F$ with proton activation represents a new class of therapeutics.

US011396523B2

(12) United States Patent
Rich et al.

(10) Patent No.: US 11,396,523 B2
(45) Date of Patent: Jul. 26, 2022

(54) PROTON ACTIVATED ATOMIC MEDICINE

(71) Applicants: University of Virginia Patent Foundation, Charlottesville, VA (US); Hampton University, Hampton, VA (US)

(72) Inventors: Tyvin A. Rich, Charlottesville, VA (US); Dongfeng Pan, Charlottesville, VA (US); Mahendra D. Chordia, Charlottesville, VA (US)

(73) Assignees: University of Virginia Patent Foundation, Charlottesville, VA (US); Hampton University, Hampton, VA (US)

( * ) Notice: Subject to any disclaimer, the term of this patent is extended or adjusted under 35 U.S.C. 154(b) by 257 days.

(21) Appl. No.: 16/625,525

(22) PCT Filed: Jun. 22, 2018

(86) PCT No.: PCT/US2018/038946
§ 371 (c)(1),
(2) Date: Dec. 20, 2019

(87) PCT Pub. No.: WO2018/237241
PCT Pub. Date: Dec. 27, 2018

(65) Prior Publication Data
US 2021/0024564 A1 Jan. 28, 2021

Related U.S. Application Data

(60) Provisional application No. 62/523,349, filed on Jun. 22, 2017.

(51) Int. Cl.
*C07H 19/073* (2006.01)
*A61N 5/10* (2006.01)
(Continued)

(52) U.S. Cl.
CPC ....... *C07H 19/073* (2013.01); *A61K 31/7072* (2013.01); *A61N 5/10* (2013.01);
(Continued)

(58) Field of Classification Search
CPC combination set(s) only.
See application file for complete search history.

(56) References Cited

U.S. PATENT DOCUMENTS

| 4,938,949 A | 7/1990 | Borch et al. |
| 6,372,719 B1 | 4/2002 | Cunningham et al. |
| 2008/0170993 A1 | 7/2008 | Srinivasan et al. |

FOREIGN PATENT DOCUMENTS

CN 10157508 A 11/2009

OTHER PUBLICATIONS

Hatano et al., "Enzymatic synthesis and RNA interference of nucleosides incorporating stable isotopes into a base moiety" Bioorganic and Medicinal Chemistry vol. 23 pp. 6683-6688 http://dx.doi.org/10.1016/j.bmc.2015.09.011 (Year: 2015).*

(Continued)

*Primary Examiner* — Eric Olson
(74) *Attorney, Agent, or Firm* — Murtha Cullina LLP; Anthony P. Gangemi

(57) ABSTRACT

The present application provides compositions and methods for preparing and using "heavy" nucleotide derivatives of thymidine or uridine by replacing the oxygen atom attached to one or more of positions with non-radioactive oxygen-18 ($^{18}O$), administering it to a subject to target a tumor including incorporation into tumor cell DNA, and then treating the tumor with proton beam therapy to transmutate the $^{18}O$ to $^{18}F$, resulting in a break of the new fluorine-phosphorous bond. This chemical event destabilizes ribose-phosphate DNA back-bone and base pairing thus produce single- and double strand breaks, clusters lesions that can lead to irrepa-
(Continued)

$^{18}O$ transmutation: *Biochemical consequences!*

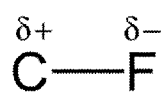

Strong dipole in an aromatic ring perturbs molecular interactions!

rable DNA damage and enhanced tumor cell killing. The atomic, chemical, and physical aspects result in the use of lower radiation doses and significantly alter acute and late morbidity of radiotherapy. Heavy thymidine and heavy uridine derivatives labeled with $^{18}O$ have been made and tested.

14 Claims, 10 Drawing Sheets

(51) Int. Cl.
    *C07B 59/00*     (2006.01)
    *A61P 35/00*     (2006.01)
    *A61K 31/7072*     (2006.01)
    *A61K 45/06*     (2006.01)

(52) U.S. Cl.
    CPC ............ *A61P 35/00* (2018.01); *C07B 59/005* (2013.01); *A61K 45/06* (2013.01); *A61N 2005/1087* (2013.01)

(56) References Cited

OTHER PUBLICATIONS

Steinhauser et al., "Quantitative imaging of subcellular metabolism with stable isotopes and multi-isotope imaging mass spectrometry" Seminars in Cell and Developmental Biology vol. 24 pp. 661-667 http://dx.doi.org/10.1016/j.semcdb.2013.05.001 (Year: 2013).*
Heck et al., "A Stable Isotope Method for Measurement of Thymidine Incorporation into DNA" Cell Tissue Kinetics vol. 10 pp. 111-119 (Year: 1977).*
Fenselau et al., "Stable Isotope Analysis by Fast-Atom Bombardment Labeling of Udpglucuronic Acid" Drug Metabolism and Disposition vol. 10 No. 4 pp. 316-318 (Year: 1982).*
Cho et al., "Feasibility of hydrogel fiducial markers for in vivo proton range verification using PET" Physics in Medicine & Biology vol. 61 pp. 2162-2176 doi:10.1088/0031-9155/61/5/2162 (Year: 2016).*
Wang, Meiyao; Shen, Yang; Turko, Illarion V.; Nelson, Daniel C; Li, Shuwei; 1. Determining Carbapenemase Activity with 18O Labeling and Targeted Mass Spectrometry. Analytical Chemistry (Washington, DC, United States) (2013), 85(22), 11014-11019.
Bergmann, Dominik; Huebner, Florian; Humpf, Hans-Ulrich; Stable Isotope Dilution Analysis of Small Molecules with Carboxylic Acid Functions Using 18O Labeling for HPLC-ESI-MS/MS: Analysis of Fumonisin B 1. Journal of Agricultural and Food Chemistry (2013), 61(33), 7904-7908.
Moore, Ronald J.; Schepmoes, Athena A.; Xiao, Wenzhong; Moldawer, Lyle L.; et al; Plasma Proteome Response to Severe Burn Injury Revealed by 18O-Labeled "Universal" Reference-Based Quantitative Proteomics. Journal of Proteome Research (2010), 9(9), 4779-4789.
Mori, Masaru; Abe, Kohei; Yamaguchi, Hiroaki; Goto, Junichi; Shimada, Miki; Mano, Nariyasu, Production of 18O-Single Labeled Peptide Fragments during Trypsin Digestion of Proteins for Quantitative Proteomics Using nanoLC-ESI-MS/MS. Journal of Proteome Research (2010), 9(7), 3741-3749.
Kolodziejska-Huben, Magdalena; Kaminski, Zbigniew; Paneth, Piotr; Preparation of 18O-labeled nicotinamide. Journal of Labelled Compounds & Radiopharmaceuticals (2002), 45(12), 1005-1010.
Hamasaki, Tomohiro; Matsumoto, Takahiro; Sakamoto, Naoya; Shimahara, Akiko; Kato, Shiori; Yoshitake, Ayumi; Utsunomiya, Ayumi; Yurimoto, Hisayoshi; Gabazza, Esteban C; Ohgi, Tadaaki; Synthesis of 18O-labeled RNA for application to kinetic studies and imaging. Nucleic Acids Research (2013), 41(12), e126.
H. Follmann and H.P.C. Hogenkamp, The synthesis of ribose and of adenine nucleotides containing oxygen-18. The Journal of American Chemical Society, 92:3, 1970.
Schram, Karl H.; Ratcliff, Steven; Neenan, John; Oxygen-18-labeled nucleosides. 1. A general method for the synthesis of specifically labeled pyrimidine deoxyribosides. Journal of Labelled Compounds and Radiopharmaceuticals (1982), 19(3), 399-404.
Solsten, R. Thomas; McCloskey, James A.; Schram, Karl H. Oxygen-18-labeled nucleosides. 2. A general method for the synthesis of specifically labeled pyrimidine ribonucleosides. Nucleosides & Nucleotides (1982), 1(1), 57-64.
Wiebe, L., Applications of Nucleoside-based Molecular Probes for the in vivo Assessment of Tumour Biochemistry using Positron Emission Tomography (PET). Brazilian Archives of Biology and Technology (2007), 50:3:445-459.
Jongmin Cho, Geoffrey Ibbott, Michael Gillin, Calos Gonzalez-Lepera, Uwe Titt, Harald Paganetti, Matthew Kerr, and Osama Mawlawi, Feasibility of proton-activated implantable markers for proton range verification using PET. Phys Med Biol. Nov. 7, 2013; 58(21): 7497-7512.
Stephen F. Altschul, Thomas L. Madden, Alejandro A. Schaffer, Jinghui Zhang, Zheng Zhang, Webb Miller and David J. Lipman, Gapped BLAST and PSI-BLAST: a new generation of protein database search programs. Nucleic Acids Research, 1997, vol. 25, No. 17 3389-3402.
Samuel Karlin and Stephen F. Altschul, Methods for assessing the statistical significance of molecular sequence features by using general scoring schemes. Proc. Natl. Acad. Sci. USA Mar. 1990 vol. 87, pp. 2264-2268.
Samuel Karlin and Stephen F. Altschul, Applications and statistics for multiple high-scoring segments in molecular sequences. Proc. Natl. Acad. Sci. USA Jun. 1993 vol. 90, pp. 5873-5877.
Stephen F. Altschul, Warren Gish, Webb Miller, Eugene W. Myers and David J. Lipman, Basic Local Alignment Search Tool. J. Mol. Biol., 1990, 215, 403-410.
Akihiko Hatano, Mitsuya Shiraishi, Nanae Terado, Atsuhiro Tanabe, and Kenji Fukuda, Enzymatic synthesis and RNA interference of nucleosides incorporating stable isotopes into a base moiety. Biorganic & Medicinal Chemistry, Sep. 7, 2015, vol. 23 6683-6688.
International search report corresponding to PCT/US2018/38946 dated Oct. 30, 2018.
Schubert, Ernst M.; Schram, Karl H; Oxygen-18-labeled nucleosides. 3. Preparation and mass spectra metric evaluation of 18O2-labeled 1-(β-0-arabinofuranosyl)cytosine and -uracil. Journal of Labelled Compounds and Radiopharmaceuticals (1982), 19(8), 929-35.
Database CAPLUS [Online] Chemical Abstracts Service, Columbus, Ohio, US: 1991, Schubert et al., XP55769333, Database accession No. 1991: 583782.
Database CAPLUS [Online] Chemical Abstracts Service, Columbus, Ohio, US: 1998, XP55769666, Database accession No. 1998: 62758.
Supplementary European search report corresponding to EP18819570 dated Jan. 28, 2021.

* cited by examiner

$^{18}O$ transmutation: *Biochemical consequences!*
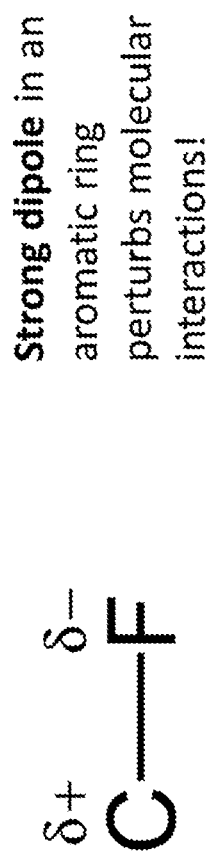
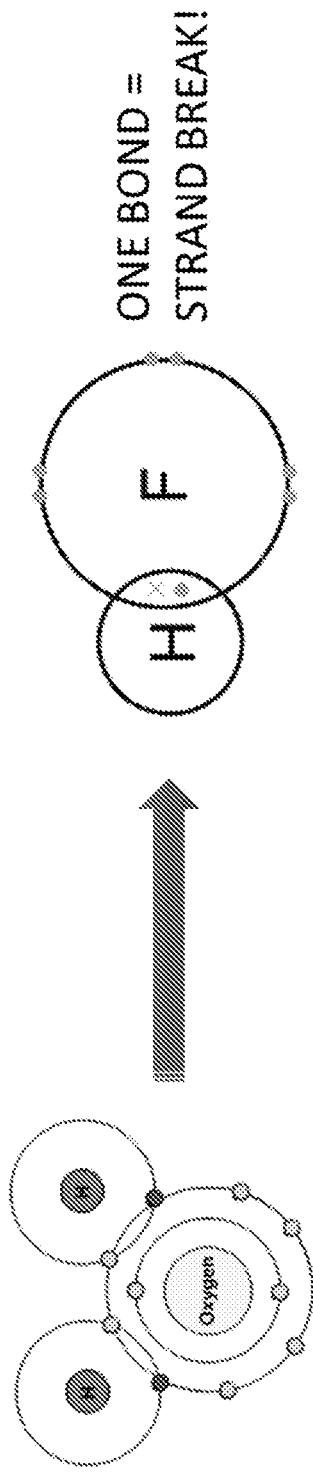
Strong dipole in an aromatic ring perturbs molecular interactions!
ONE BOND = STRAND BREAK!
FIG. 3

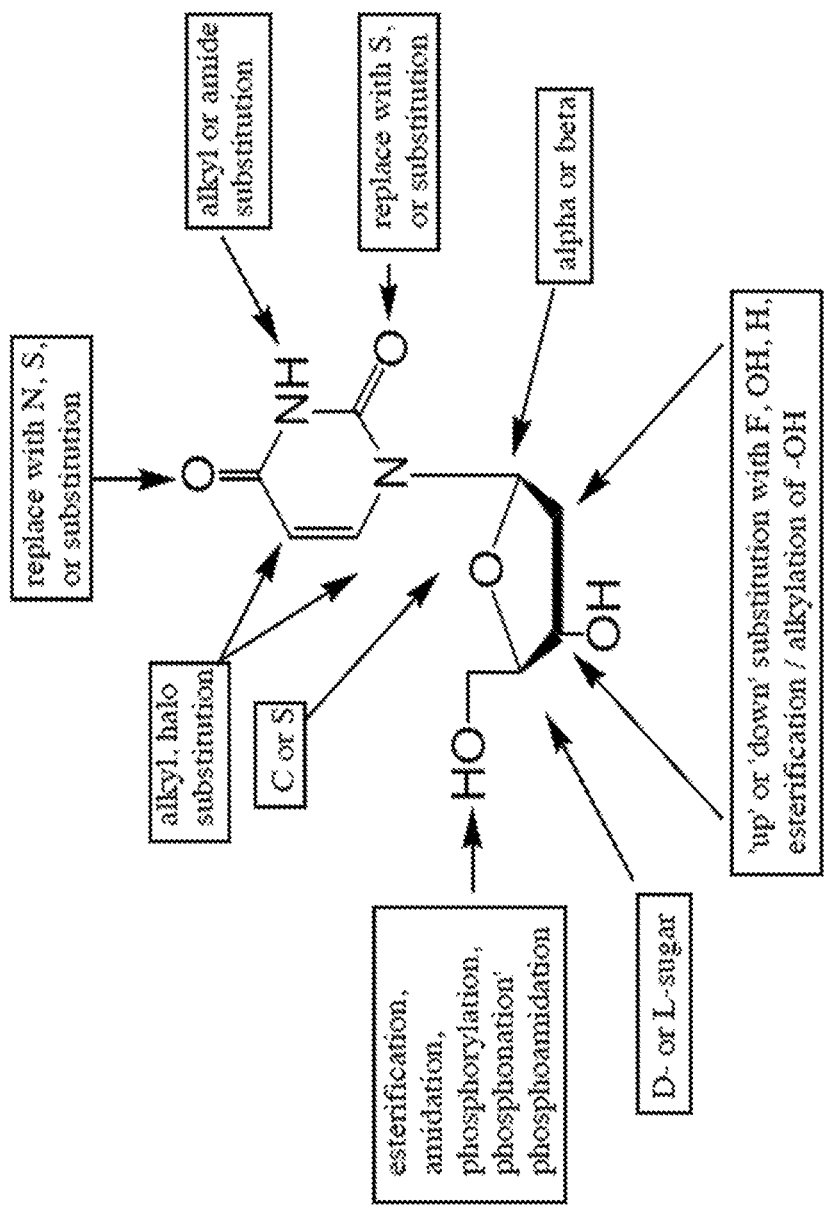
FIG. 4. – Sites for chemical modification of pyrimidine nucleosides, using 2' deoxyuridine as a model.

Example of heavy oxygen 18 labeled Nucleotides
O¹⁸ oxygen atom is defined with red color
Synthesis of Singly O¹⁸ labeled C2 and C5'-O18 thymidines
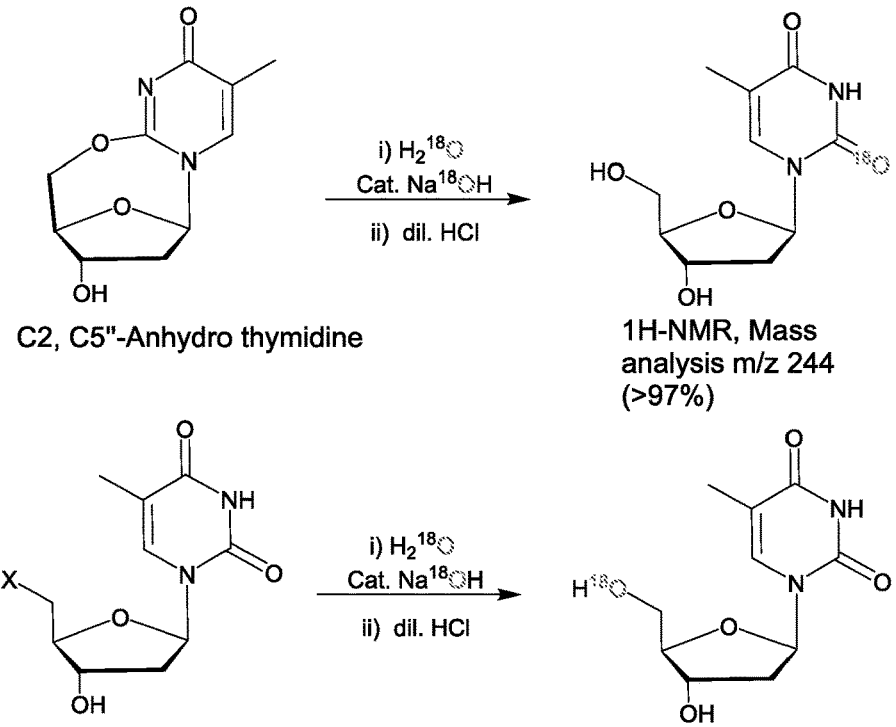
Synthesis of Singly O¹⁸ labeled C2 and C5'-O¹⁸ 2'-deoxy-uridines
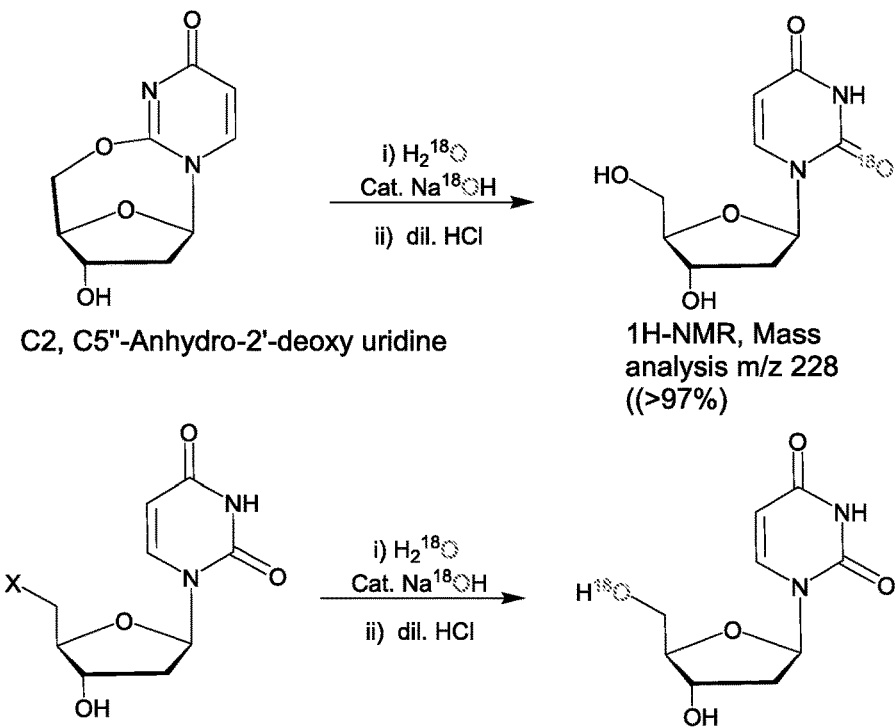
FIG. 6

Example of heavy oxygen 18 labeled thymidine derivatives
Singly O[18] labeled synthetic thymidine derivatives
O[18] oxygen atom is defined with red color
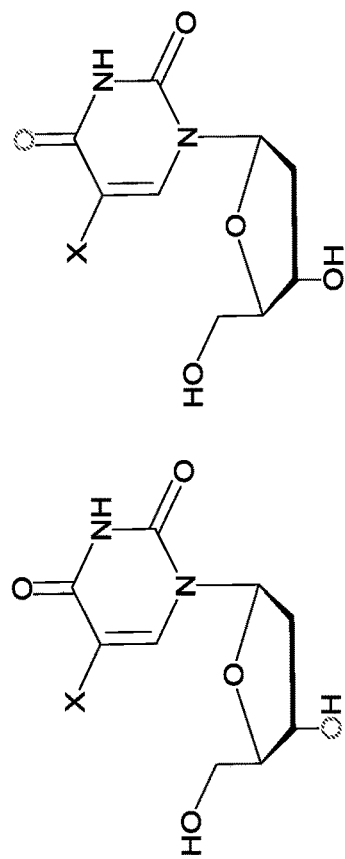
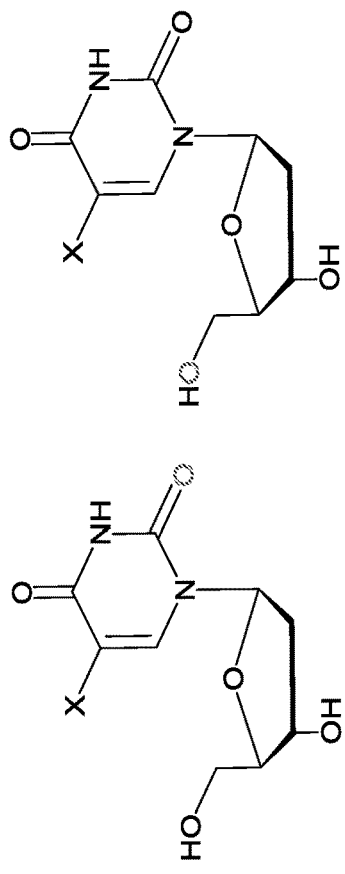
X = halogens e.g. F, Cl, Br, I or CF$_3$ or any other group such OH, NH2 OR, N$_3$, CH$_2$X
FIG. 7

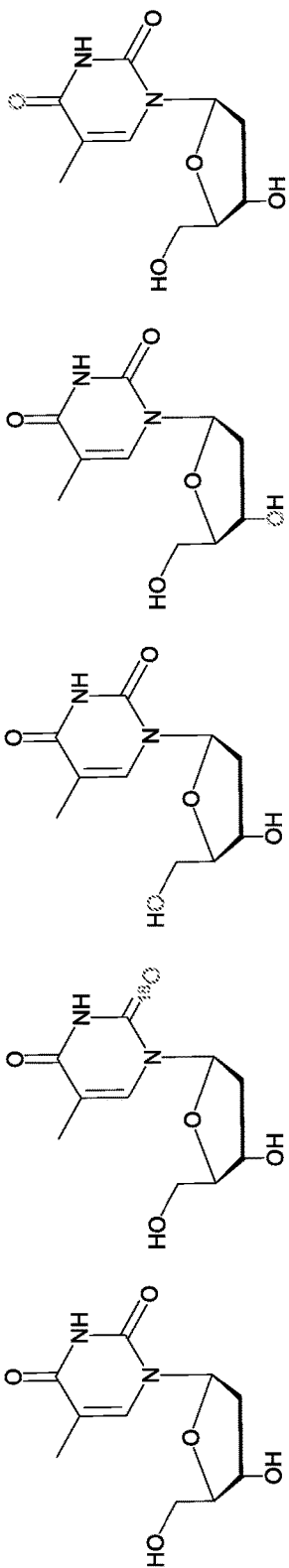
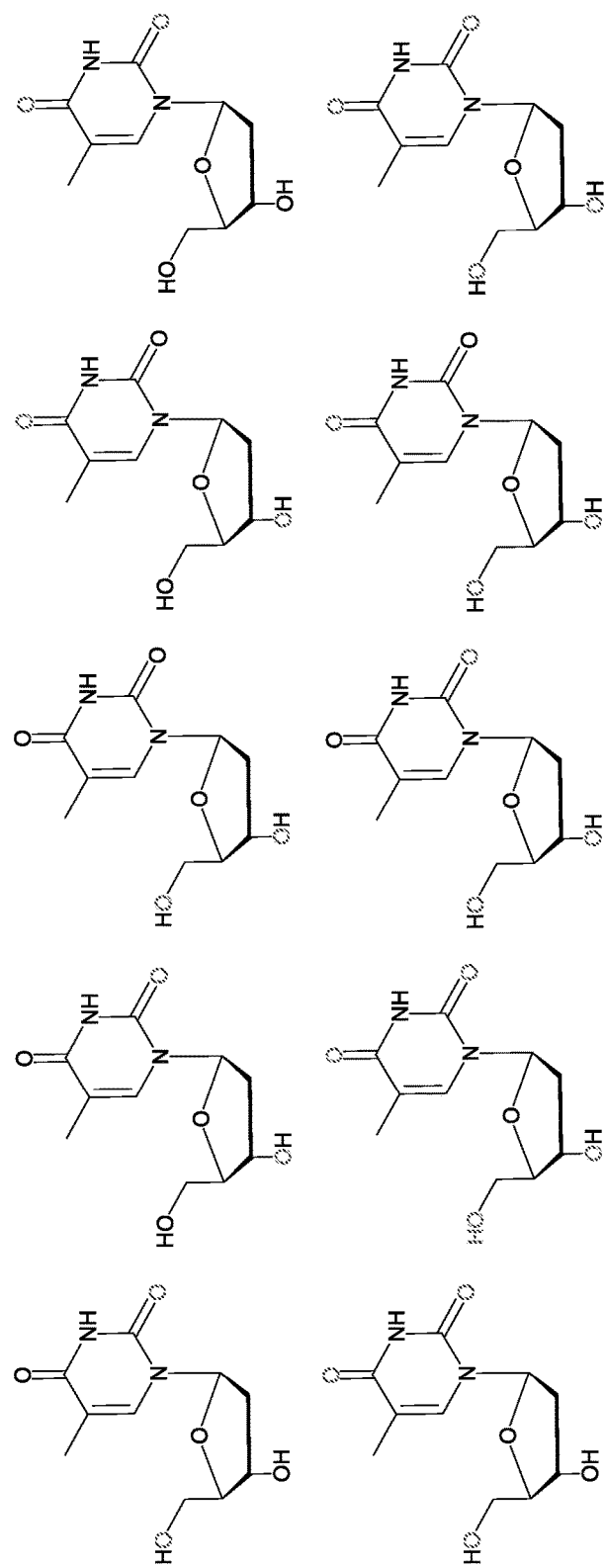
FIG. 8

PROTON ACTIVATED ATOMIC MEDICINE

CROSS REFERENCE TO RELATED APPLICATIONS

This application claims priority under 35 U.S.C. § 119(e) to U.S. Provisional Application Ser. No. 62/523,349 filed Jun. 22, 2017, the disclosure of which is incorporated by reference in its entirety herein.

BACKGROUND

Radiation therapy, whether used alone or combined with other treatments, is an important treatment for many cancers. More than half of all cancer patients receive one or more courses of radiation therapy as part of their treatment. However, in radiation therapy, large amounts of energy are directed at cancer cells to disrupt growth and x-rays are the type of energy found in conventional radiation therapy. Unfortunately, both healthy and cancerous cells are affected by radiation, so the goal is to radiate only the targeted cancer cells.

Both proton therapy and traditional radiation treat malignancies the same way: by inhibiting the growth of cancer cells. Proton beam therapy reduces many of the issues associated with conventional radiation therapy. Protons carry the energy in proton therapy and the protons are raised to a high energy level using a particle accelerator. An advantage of proton therapy is that proton beams stop after releasing their energy within a target and the beam can be more finely controlled, allowing for higher doses of radiation to be used because the tumor can be more specifically targeted. Thus, surrounding healthy tissue is less affected than when x-rays are used. Protecting healthy tissue is particularly important when the patient is a child. Children can have the greatest long-term harm from conventional radiation therapy since their organs are still developing. Delayed effects of X-ray therapy in children can include growth problems, hearing and vision loss, radiation-induced cancers, and heart disease.

Proton therapy is typically used for tumors that have not spread to other parts of the body and is effective in treating many types of cancer. Proton therapy may be most valuable in the treatment of tumors including, but not limited to, brain, breast, bone, gastrointestinal tract, prostate, and pediatric cancers.

Because there are not many cancer centers utilizing proton beam therapy, its full potential has not yet been realized.

There is a long felt need in the art for compositions and methods useful for diagnosing and treating diseases and disorders encompassing excessive cell proliferation, particularly cancer. The present invention satisfies these needs.

SUMMARY OF THE INVENTION

The present application discloses novel purines and pyrimidines in which oxygen atoms are replaced with heavy oxygen and are used in proton beam therapy and in diagnostics. The predominant literature on $^{18}O$ deals with its precursor role in the production of diagnostic agents like $^{18}F$-deoxyglucose for clinical PET scanning that now can be done with mini-cyclotrons in community hospitals. The literature shows that $^{18}O$ incorporates well into HT analogues (97%); evolving methods with this isotope currently includes biomarkers for oncology opening the possibility for the creation of other tagged heavy analogues.

In one aspect, the oxygen atoms attached, for example, at the 3' or 5' position of the ribose structure are replaced with heavy oxygen (oxygen-18/$^{18}O$). Four different sites of labeling are disclosed herein. In one aspect, the oxygen atoms at both positions are replaced. In another aspect, the oxygen atom at the 2 position on a thymine ring is replaced with $^{18}O$. In one aspect, at least two oxygen atoms are replaced with $^{18}O$. In one aspect, all oxygen atoms are replaced with $^{18}O$. In one aspect, heavy thymidine is prepared and used.

In one aspect, the present application discloses compositions and methods useful for making and using non-natural nucleotide derivatives. In one aspect, the non-natural nucleotides are modified with $^{18}O$. In one aspect, the non-natural derivatives are deuterated. In one aspect, the non-natural nucleotides are modified with $^{18}O$ and are deuterated.

Compounds of the invention are administered to a subject for use as a diagnostic/imaging agent and/or for therapeutic use. In one aspect, after a compound has incorporated into cellular DNA the $^{18}O$ targeting agent is activated by proton treatment. In one aspect, the cell is a cancer cell. In one aspect, the cell is killed.

In one embodiment, the proton treatment activates the $^{18}O$ targeting agent and the ensuing particle-nuclear reaction transmutates $^{18}O$ into $^{18}F$. In one aspect, a proton beam is used to induce the transmutation. In one aspect, once transmutation occurs the new atomic state results in a chemical break of the fluorine-phosphorous bond. Breaking the bond leads to destabilization of the ribose-phosphate DNA ladder or altered based pairing, resulting in, inter alia, altered DNA damage repair and increased cell death.

It is disclosed herein that a nucleotide can be selectively substituted at the atomic level using heavy oxygen, that it incorporates into DNA, and it magnifies the dose effect by a significant amount. When combined with proton beam therapy there is unexpectedly an even greater increase in sensitivity of cells to the treatment.

In one embodiment, once transmutation occurs, $^{18}F$ can be detected and measured using PET. $^{18}F$ is a useful imaging probe.

A tumor being treated can be imaged before or after administration of an $^{18}O$ labeled compound of the invention. One of ordinary skill in the art can determine which type of imaging to perform. A tumor can also be monitored before and after treatment using imaging procedures.

The present application discloses derivatives of both thymidine and uridine that have been labeled at one or more positions with heavy oxygen ($^{18}O$).

Thymidine has the structure:

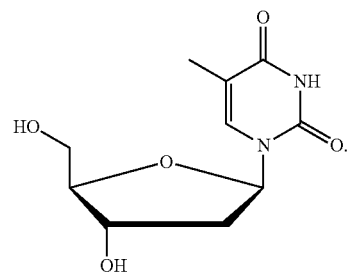

In one embodiment, the present application discloses generic formulas comprising structures of useful compounds of the invention. Four different oxygen sites for substitution with $^{18}O$ are disclosed and provided below for thymidine derivatives. In one aspect, the present application provides compounds selected from the formula consisting of:

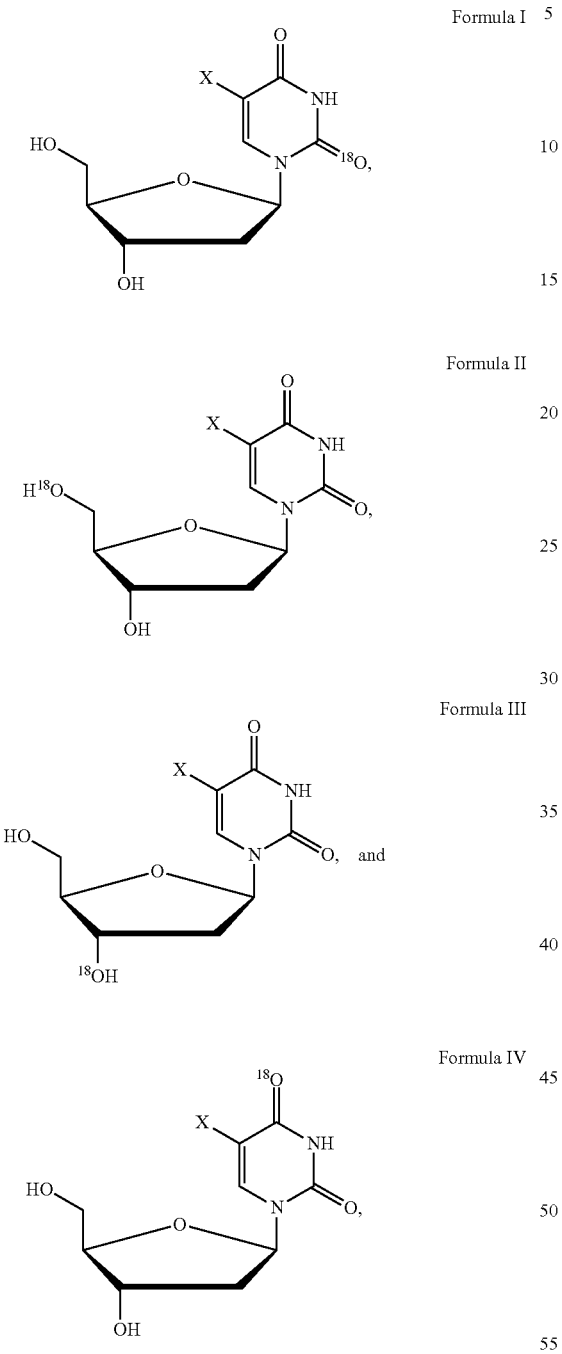

wherein:

X is selected from the group consisting of CH₃, halogen, CF3, OH, NH₂, OR, N₃, and CH₂X; and R is selected from the group consisting of alkyl, alkene, alkyne, and aryl.

Halogens can be F, Cl, Br, or I. When fluorine is used, it can be present in a compound as CF, CF₂ or CF₃.

In one embodiment, a compound is deuterated.

Some singly $O^{18}$ labeled thymidines of the invention include:

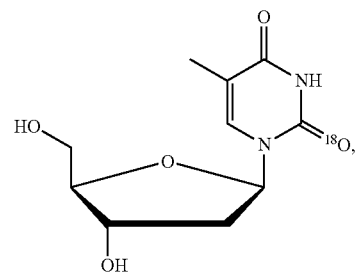

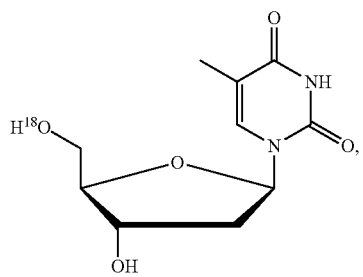

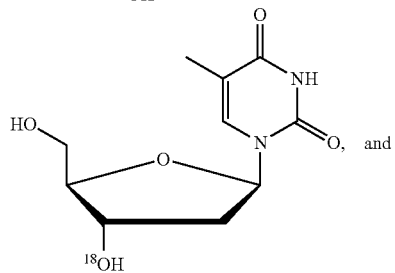

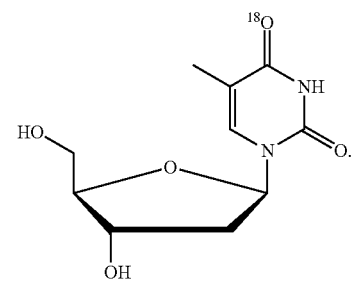

Some thymidines labeled with multiple $^{18}O$ molecules include:

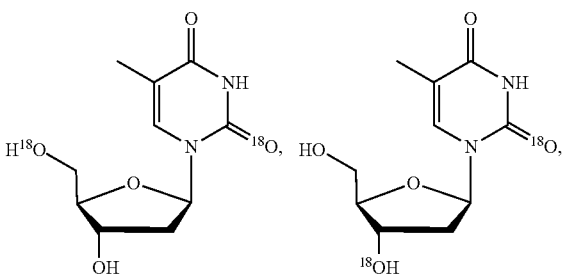

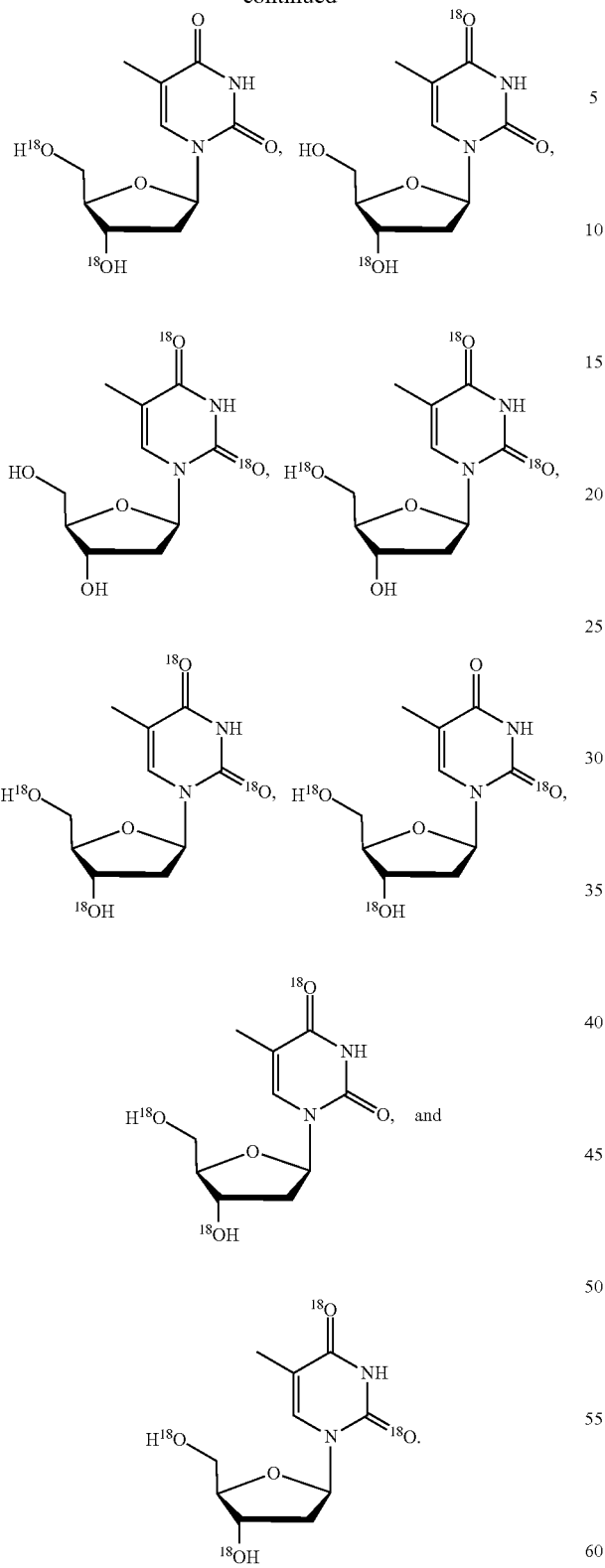
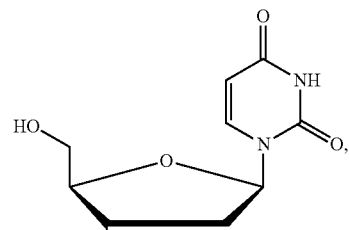
2'-deoxyuridine
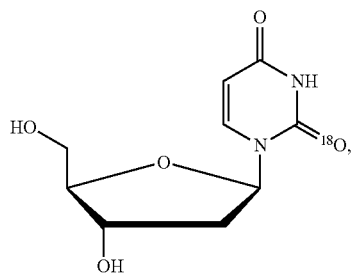
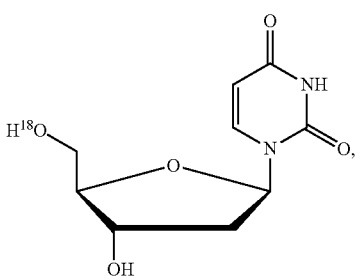
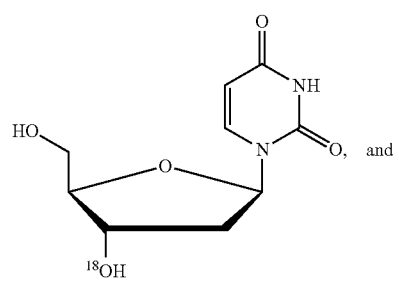
and
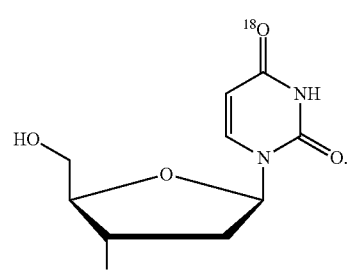
Also provided are examples of heavy oxygen 18 labeled 2'-deoxy uridinethymidine (also referred to as 2'-deoxyuridine). The same four sites comprising oxygen can be substituted with $^{18}O$ as for thymidine. Singly $^{18}O$ labeled uridines, include, but are not limited to:

Some uridines that are multiply labeled with $^{18}O$ include:

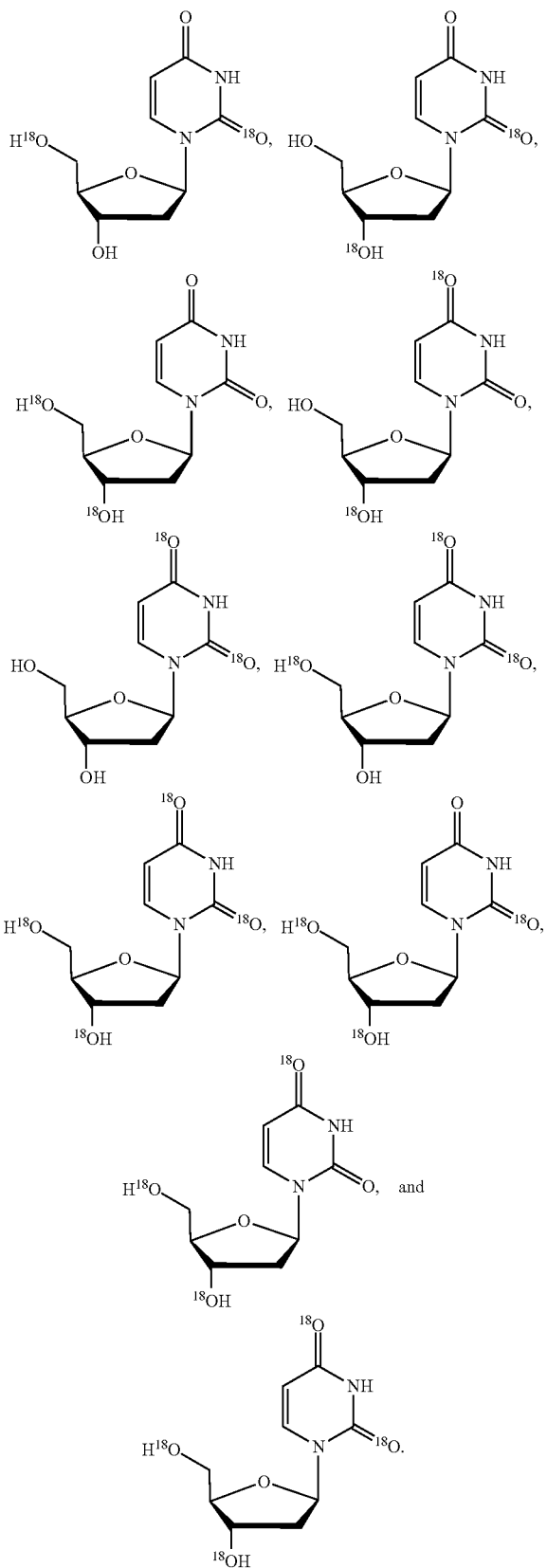

In one embodiment, the present application provides for deuterated modifications to the compounds of the invention.

Proton therapy as disclosed herein when using a compound of the invention can be used in combination with other treatments such as conventional X-ray radiation, chemotherapy, and surgery. Based on the present disclosure, one of ordinary skill in the art can determine if a combination treatment should be used.

The present application provides methods for administering $^{18}O$ labeled compounds to a subject, subjecting the subject to a proton beam and converting the $^{18}O$ to radioactive $^{18}F$. Radioactive $^{18}F$ can then be detected and measured in the subject. PET imaging can be used to detect tumors that are present, provide diagnoses, quantify the label present, and can be used in follow up procedures to monitor treatment.

When treating a subject, exposure to a proton beam can be from about 2 to about 100 Gy. In one aspect, treatment is about 2, 6, 8, 10, 20, 30, 40, 50, 50, 70, 80, 90, 100, 110, 120, 130, 140, and 150 Gy. In one aspect, fractional doses are about 2-10 Gy. In one aspect, total doses are about 50-150 Gy. In one aspect, proton beam irradiation is with 160 MeV protons single fraction. Accelerators used for proton therapy typically produce protons with energies in the range of 70 to 250 MeV.

A treatment regimen may require about five treatments for about 4 to eight weeks. The physician can establish the regimen based on criteria such as the type of cancer, its location, and the age, sex, and health of the subject.

In one embodiment, prior to treatment the tumor is imaged using, for example, CT to create a virtual model of the tumor.

After administration of an $^{18}O$ labeled compound to a subject, it can be used for imaging before being subjected to a proton beam.

In one embodiment, an $^{18}O$ labeled compound of the invention is subjected to a proton beam prior to administration to a subject. In one aspect, the $^{18}O$ is transmutated to a radioactive $^{18}F$.

In one embodiment derivatives of thymidine or uridine are made and used comprising a $^{19}F$ label. In one embodiment, subjecting the derivative to a proton beam converts $^{19}F$ to $^{18}F$.

Based on the disclosure provided herein, the present invention encompasses the beginning of Proton-Activated Atomic Medicine (PAAM) using design science to provide new molecules for diagnosis and treatment, and is useful as a new radiation therapy paradigm that is better than prior proton beam therapy and diagnosis and the use of conventional irradiation. The compositions and methods encompass:

transmutation: imaging and chemical consequences;
target: atomic sites in DNA and RNA;
chemistry achievable at reasonable cost;
physiologic doses, non-radioactive, non-toxic;
proliferation specific incorporation: cancer greater than normal tissues; and
proton dose distribution will activate cancer and avoid rapidly proliferating tissues.

In one embodiment, the present application provides compositions and methods for killing proliferating cancer cells. In one aspect, the method comprises contacting a proliferating cancer cell with an effective amount of an $^{18}O$ labeled compound of the invention and allowing the compound to incorporate into the DNA of the proliferating cancer cells, followed by subjecting the proliferating cancer cells to proton beam therapy.

The types of cancer typically subjected to proton beam therapy are encompassed by the methods of the invention and include, but are not limited to, brain, breast, bone, gastrointestinal tract, prostate, and pediatric tumors and cancer cells.

The present invention encompasses a kit comprising at least one $^{18}$O labeled compound of the invention, a pharmaceutically acceptable carrier, an applicator, and an instructional material for the use thereof.

Various aspects and embodiments of the invention are described in further detail below.

BRIEF DESCRIPTION OF THE DRAWINGS

FIG. 3 provides a schematic representation of $^{18}$O transmutation and the chemical consequences of the transmutation.

FIG. 4 provides a schematic representation of sites for chemical modification of pyrimidine nucleosides and types of modifications that can be made at those sites, using 2' deoxyuridine as a model. (based on FIG. 6 from Wiebe, Brazilian Archives of Biology and Technology, 2007, 50:3: 445-459).

FIG. 5, comprising FIGS. 5A and 5B, provides schematically a conceptual depiction of Proton Activated Atomic Medicine.

FIG. 6 demonstrates the synthesis of heavy oxygen 18 labeled nucleotides.

FIG. 7 provides examples of heavy oxygen 18 singly labeled thymidine derivatives of the invention, comprising a site for various sub stituents, wherein X can be $CH_3$, a halogen, $CF_3$, OH, $NH_2$, OR, $N_3$, or $CH_2X$. Halogens can be F, Cl, Br, or I. R is selected from the group consisting of alkyl, alkene, alkyne, and aryl. Heavy oxygen 18 is demonstrated in red.

FIG. 8 provides examples of specific heavy oxygen 18 labeled thymidines of the invention. Some are singly labeled and some comprise two or more $^{18}$Os. Heavy oxygen 18 is demonstrated in red.

DETAILED DESCRIPTION

Abbreviations and Acronyms

Figure 1:
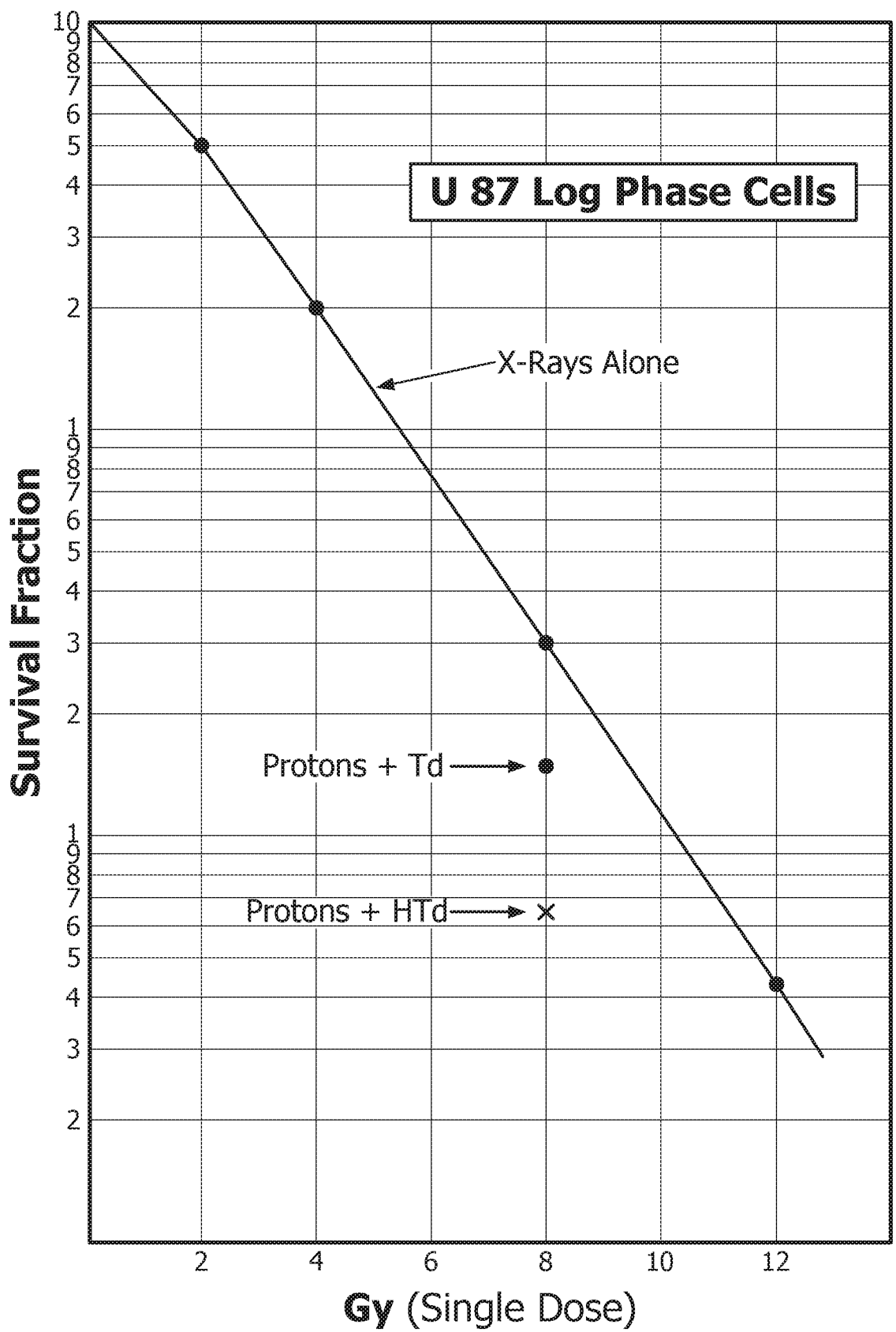
FIG. 1 is a graphic representation of the dose of irradiation (x-axis) versus the log survival fraction (y-axis) of log phase U87 human glioblastoma cells. Three groups were used. The solid line is the result of treatment with conventional x-rays. There are about 2 logs of cell kill with 10 Gy with x rays. Shown are the survival fractions with 8 Gy of proton irradiation either alone or combined with normal thymidine where cells were exposed with a 0.5 micro molar concentration in vitro for 96 hours prior to proton beam treatment. Below that is shown the survival fraction for the same concentration and duration of exposure with "heavy" thymidine. This molecule is synthesized by replacing the 2 position of the aromatic ring of the nitrogenous base with oxygen-18. When these cells are treated with protons, there is a chemical transmutation at the atomic level where upon the oxygen-18 atom is changed into radioactive fluorine-18. This causes a chemical change at the molecular level and results in greater cell kill. Td-thymidine; HTd-heavy thymidine.

CT—computerized tomography (also referred to as computerized axial tomography or CAT)
FDG—fluorodeoxyglucose
Gy—gray, the international system (SI) unit of radiation dose, expressed as absorbed energy per unit mass of tissue; Gy has replaced "rad"
GyE—gray equivalent
HT—heavy thymidine, also referred to as HTd
$^{18}$O—oxygen-18
PAAM—proton activated atomic medicine
PBT—proton beam therapy
PET—positron emission tomography
SOBP—spread-out bragg peak
Td—thymidine Definitions In describing and claiming the invention, the following terminology will be used in accordance with the definitions set forth below. Unless defined otherwise, all technical and scientific terms used herein have the commonly understood meaning by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

2'-deoxyuridine is also referred to as (2-Deoxy-β-D-ribofuranosyl)uracil and uracil deoxyriboside.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

The term "adult" as used herein, is meant to refer to any non-embryonic or non-juvenile subject. For example the term "adult adipose tissue stem cell," refers to an adipose stem cell, other than that obtained from an embryo or juvenile subject.

As used herein, an "agonist" is a composition of matter which, when administered to a mammal such as a human, enhances or extends a biological activity attributable to the level or presence of a target compound or molecule of interest in the mammal.

A disease or disorder is "alleviated" if the severity of a symptom of the disease, condition, or disorder, or the frequency with which such a symptom is experienced by a subject, or both, are reduced.

As used herein, "alleviating a disease or disorder symptom," means reducing the severity of the symptom or the frequency with which such a symptom is experienced by a subject, or both.

An "antagonist" is a composition of matter which when administered to a mammal such as a human, inhibits a biological activity attributable to the level or presence of a compound or molecule of interest in the mammal.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

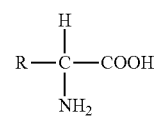

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog", or "analogue", of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antibody", as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain", as used herein, refers to the larger of the two types of polypeptide chains present in all antibody molecules.

An "antibody light chain", as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

"Anti-proliferative," as used herein, refers to the ability of a compound to impede or inhibit cell proliferation. As such, the compound may act directly on a cell or may act indirectly. For example, in the context of cancer, a cancer cell can be inhibited from proliferating by depriving it of blood supply. The term "anti-proliferative" does not refer to a particular mechanism by which proliferation is inhibited or impeded.

As used herein the term "anti-tumor agent" relates to agents known in the art that have been demonstrated to have utility for treating neoplastic disease. For example, antitumor agents include, but are not limited to, antibodies, toxins, chemotherapeutics, enzymes, cytokines, radionuclides, photodynamic agents, and angiogenesis inhibitors. Toxins include ricin A chain, mutant Pseudomonas exotoxins, diphtheria toxoid, streptonigrin, boamycin, saporin, gelonin, and pokeweed antiviral protein. Chemotherapeutics include 5-fluorouracil (5-FU), daunorubicin, cisplatinum, bleomycin, melphalan, taxol, tamoxifen, mitomycin-C, and methotrexate as well as any of the compounds described in U.S. Pat. No. 6,372,719 (the disclosure of which is incorporated herein by reference) as being chemotherapeutic agents. Radionuclides include radiometals. Photodynamic agents include porphyrins and their derivatives.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, sputum, mucus, phlegm, tissues, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, and urine. One of skill in the art will understand the type of sample needed.

A "biomarker" or "marker" is a specific biochemical in the body which has a particular molecular feature that makes it useful for measuring the progress of disease or the effects of treatment, or for measuring a process of interest.

The term "cancer", as used herein, is defined as proliferation of cells whose unique trait—loss of normal controls—results in unregulated growth, lack of differentiation, local tissue invasion, and metastasis. Examples include, but are not limited to, carcinomas, sarcomas, leukemias, glioblastoma, melanoma, breast cancer, prostate cancer, ovarian cancer, uterine cancer, cervical cancer, skin cancer, pancreatic cancer, colorectal cancer, renal cancer, and lung cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize), as well as any of a number of characteristic structural and/or molecular features. A "cancerous" or "malignant cell" is understood as a cell having specific structural properties, lacking differentiation and being capable of invasion and metastasis. Examples of cancers are, breast, lung, brain, bone, liver, kidney, colon, and prostate cancer. (see DeVita, V. et al. (eds.), 2001, Cancer Principles and Practice of Oncology, 6th. Ed., Lippincott Williams & Wilkins, Philadelphia, Pa.; this reference is herein incorporated by reference in its entirety for all purposes).

"Cancer-associated" refers to the relationship of a nucleic acid and its expression, or lack thereof, or a protein and its level or activity, or lack thereof, to the onset of malignancy in a subject cell. For example, cancer can be associated with expression of a particular gene that is not expressed, or is expressed at a lower level, in a normal healthy cell. Conversely, a cancer-associated gene can be one that is not expressed in a malignant cell (or in a cell undergoing transformation), or is expressed at a lower level in the malignant cell than it is expressed in a normal healthy cell.

As used herein, the term "carrier molecule" refers to any molecule that is chemically conjugated to the antigen of interest that enables an immune response resulting in antibodies specific to the native antigen.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

The term "competitive sequence" refers to a peptide or a modification, fragment, derivative, or homolog thereof that competes with another peptide for its cognate binding site.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "complex", as used herein in reference to proteins, refers to binding or interaction of two or more proteins. Complex formation or interaction can include such things as binding, changes in tertiary structure, and modification of one protein by another, such as phosphorylation.

A "compound", as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

A "computer-readable medium" is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

A "pathoindicative" cell is a cell which, when present in a tissue, is an indication that the animal in which the tissue is located (or from which the tissue was obtained) is afflicted with a disease or disorder.

A "pathogenic" cell is a cell which, when present in a tissue, causes or contributes to a disease or disorder in the animal in which the tissue is located (or from which the tissue was obtained).

A tissue "normally comprises" a cell if one or more of the cell are present in the tissue in an animal not afflicted with a disease or disorder.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "diagnosis" refers to detecting cancer or a risk or propensity for development of cancer, for the types of cancer encompassed by the invention. In any method of diagnosis exist false positives and false negatives. Any one method of diagnosis does not provide 100% accuracy.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

"Element" refers to a species of atoms; all atoms with the same number of protons in the atomic nucleus—a pure chemical substance composed of atoms with the same number of protons in the atomic nucleus "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "effector domain" refers to a domain capable of directly interacting with an effector molecule, chemical, or structure in the cytoplasm which is capable of regulating a biochemical pathway.

As used in the specification and the appended claims, the terms "for example", "for instance," "such as", "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein. An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly 5 amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

"Gamma rays" (gamma irradiation) refers to a stream of high-energy electromagnetic radiation given off by an atomic nucleus undergoing radioactive decay. The energies of gamma rays are higher than those of X-rays; thus, gamma rays have greater penetrating power.

"Half-life" (radioactive) refers to the time interval that it takes for the total number of atoms of any radioactive isotope to decay and leave only one-half of the original number of atoms.

"Homologous" as used herein, refers to the subunit sequence similarity between two polymeric molecules, e.g., between two nucleic acid molecules, e.g., two DNA molecules or two RNA molecules, or between two polypeptide molecules.

When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means. Compounds or agents of the invention can be administered to a subject by these means when appropriate.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

"Isotope" refers to one of two or more species of atoms of a given element (having the same number of protons in the nucleus) with different atomic masses (different number of neutrons in the nucleus). The atom can either be a stable isotope or a radioactive isotope.

"Isotopically labeled" refers to a mixture of an isotopically unmodified compound with one or more analogous isotopically substituted compound(s).

A "ligand" is a compound that specifically binds to a target receptor or target molecule.

A "receptor" or target molecule is a compound that specifically binds to a ligand.

A ligand or a receptor "specifically binds to" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "measuring the level of expression" or "determining the level of expression" as used herein refers to any measure or assay which can be used to correlate the results of the assay with the level of expression of a gene, mRNA, miRNA, SNPs, or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

What is meant by a "method of treating a tumor using proton beam therapy in a subject in need thereof" is meant treating cancers that are susceptible to using proton beam therapy based on their size, location, etc.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Operably linked" refers to a juxtaposition wherein the components are configured so as to perform their usual function. Thus, control sequences or promoters operably linked to a coding sequence are capable of effecting the expression of the coding sequence. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

As used herein, the term "peptide ligand" (or the word "ligand" in reference to a peptide) refers to a peptide or fragment of a protein that specifically binds to a molecule, such as a protein, carbohydrate, and the like. A receptor or binding partner of the peptide ligand can be essentially any type of molecule such as polypeptide, nucleic acid, carbohydrate, lipid, or any organic derived compound. Specific examples of ligands are peptide ligands of the present inventions.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

"Pharmaceutically acceptable" means physiologically tolerable, for either human or veterinary application.

As used herein, "pharmaceutical compositions" include formulations for human and veterinary use.

"Plurality" means at least two.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

"Positron" refers to the antimatter counterpart of the electron, with a mass identical to that of the electron and an equal but opposite (positive) charge.

"Positron emission tomography (PET) scan" refers to an imaging technique that is used to observe metabolic activity within the body. The system detects pairs of gamma rays emitted indirectly by a radioactive isotope used as a tracer, which emits positrons and which is introduced into the body on a biologically-active molecule. Three-dimensional images of the concentration of the radioactive isotope within the body are then constructed by computer analysis. The imaging often is performed with an X-ray CT scan in the same instrument.

"Proton" refers to an elementary particle having a rest mass of about $1.673 \times 10^{-27}$ kg, slightly less than that of a neutron, and a positive electric charge equal and opposite to that of the electron. The number of protons in the nucleus of an atom is the atomic number.

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder. Unless the term "treatment" or "treating" is used with the term preventive or prophylactic treatment it should not be construed to include such in less it is clear by the context.

A "prophylactic" treatment is a treatment administered to a subject who does not exhibit signs of a disease or injury or exhibits only early signs of the disease or injury for the purpose of decreasing the risk of developing pathology associated with the disease or injury. The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., The Peptides, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

"Radioactive decay" refers to the process by which unstable (or radioactive) isotopes lose energy by emitting alpha particles (helium nuclei), beta particles (positive or negative electrons), gamma radiation, neutrons or protons to reach a final stable energy state.

"Radioactive isotope (radioisotope)" refers to an atom for which radioactive decay has been experimentally measured (also see half-life).

The term "regulate" refers to either stimulating or inhibiting a function or activity of interest.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds, or it means that one molecule, such as a binding moiety, e.g., an oligonucleotide or antibody, binds preferentially to another molecule, such as a target molecule, e.g., a nucleic acid or a protein, in the presence of other molecules in a sample.

The terms "specific binding" or "specifically binding" when used in reference to the interaction of a peptide (ligand) and a receptor (molecule) also refers to an interaction that is dependent upon the presence of a particular structure (i.e., an amino sequence of a ligand or a ligand binding domain within a protein); in other words the peptide comprises a structure allowing recognition and binding to a specific protein structure within a binding partner rather than to molecules in general. For example, if a ligand is specific for binding pocket "A," in a reaction containing labeled peptide ligand "A" (such as an isolated phage displayed peptide or isolated synthetic peptide) and unlabeled "A" in the presence of a protein comprising a binding pocket A the unlabeled peptide ligand will reduce the amount of labeled peptide ligand bound to the binding partner, in other words a competitive binding assay.

By the term "specifically binds to", as used herein, is meant when a compound or ligand functions in a binding reaction or assay conditions which is determinative of the presence of the compound in a sample of heterogeneous compounds.

"Stable isotope" refers to an atom for which no radioactive decay has ever been experimentally measured.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease. Unless the term "treatment" or "treating" is used with the term "preventive" or "prophylactic" it should not be construed to include such in less it is clear by the context.

By the term "x-rays" is meant electromagnetic radiation with a wavelength ranging from 0.01 to 10 nanometers— shorter than those of UV rays and typically longer than those of gamma rays.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_2$ alkenyl" wherein n is an integer, as used herein, represents an olefinically unsaturated branched or linear group having from two to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_2$ alkynyl" wherein n is an integer refers to an unsaturated branched or linear group having from two to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_2$ cycloalkyl" wherein n=8, represents cyclopropyl, cyclobutyl, cyclopentyl, cyclohexyl, cycloheptyl, and cyclooctyl.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. AOptionally substituted aryl@ includes aryl compounds having from zero to four substituents, and Asubstituted aryl@ includes aryl compounds having one or more substituents. The term ($C_5$-$C_8$ alkyl)aryl refers to any aryl group which is attached to the parent moiety via the alkyl group.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "halogen" or "halo" includes bromo, chloro, fluoro, and iodo.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

As used herein, the term "optionally substituted" refers to from zero to four substituents, wherein the substituents are each independently selected. Each of the independently selected substituents may be the same or different than other substituents.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

is understood to represent a mixture of the structures:

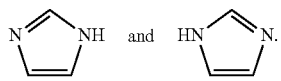 [SMILES: c1c[nH]cn1 ; "and" ; c1c[nH]cn1]

The terminology used herein is for the purpose of describing the particular versions or embodiments only, and is not intended to limit the scope of the present invention. All publications mentioned herein are incorporated by reference in their entirety.

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

In one embodiment, the invention provides a composition useful as a therapeutic for treating cancer in a subject in need thereof. In one aspect, the cancer is selected from the group consisting of melanoma, ovarian cancer, breast cancer, head and neck cancer, lung cancer, MMMT, bladder cancer, uterine cancer, endometrial cancer, liver cancer, pancreatic cancer, esophageal cancer, stomach cancer, cervical cancer, prostate cancer, adrenal cancer, lymphoma, leukemia, salivary gland cancer, bone cancer, brain cancer, cerebellar cancer, colon cancer, rectal cancer, colorectal cancer, oronasopharyngeal cancer, NPC, kidney cancer, skin cancer, basal cell carcinoma, hard palate carcinoma, squamous cell carcinoma of the tongue, meningioma, pleomorphic adenoma, astrocytoma, chondrosarcoma, cortical adenoma, hepatocellular carcinoma, pancreatic cancer, squamous cell carcinoma, and adenocarcinoma.

In one embodiment, the treatment encompasses a combination therapy.

The present invention encompasses administering the compounds of the invention based on the particular cancer being diagnosed and/or treated, its location in the subject, etc. In one aspect, a composition is administered by a route selected from the group consisting of intratumoral, parenteral, intravenous, topical, and direct. In one aspect, the compositions and methods of the invention are useful for detecting, identifying, diagnosing, and treating cancer.

Embodiments

Proton therapy treatments are nonsurgical, noninvasive and usually result in minimal side effects when combined and delivered using Pencil Beam Scanning (PBS) technology. The resulting treatment provides an even higher degree of precision, further minimizing the overall radiation exposure to healthy tissue.

The present application addresses the preparation of novel compounds and their use in proton beam therapy, diagnostics, and in theragnostics. Theragnostics is a treatment strategy that combines therapeutics with diagnostics. Coupling all of the uses together can be helpful to a physician in setting up a personalized medicine (precision medicine) approach for the patient. For example, once an $^{18}$O atom is activated in situ using the methods of the invention, it becomes a positron emitter and can be detected with a PET scan. There is no literature that teaches or suggests using a heavy thymidine labeled with $^{18}$O that is administered to a subject and is then activated by a proton beam and transmutated into $^{18}$F. That is, there is no teaching or suggestion in the art for the technology disclosed herein that allows for allowing for both treatment and imaging. The idea of the activation being preferentially happening in the patient's cancer translates into "targeted cancer detection" and may be useful, for example, as an adjunct during and after treatment to monitor the tumor.

The present compounds also have advantages over other previously used compounds for proton beam therapy, because, for example, the half-life of ubiquitous atoms studied previously to provide in vivo assessment of radiation dose localization and dosimetry is very short; whereas the half-life of activated $^{18}$F is 119 minutes. This makes $^{18}$F potentially more useful and practical for this specialized imaging procedure in the proton clinic, as well as for therapy.

The compositions include known and new compounds useful for practicing the methods of the invention, as well as methods for making the compounds. Techniques for preparing analogs, derivatives, and modifications of the generic structures of the invention are known in the art or described herein. Some examples of diseases which may be treated according to the methods of the invention are discussed herein or are known in the art. The present invention further provides methods for testing compounds of the invention. Other methods for testing compounds discovered using the methods of the invention are either described herein or are known in the art.

When a halogen is added to a derivative, they can be F, Cl, Br, or I. When fluorine is used, it can be present in a compound as CF, $CF_2$, or $CF_3$.

The amount of time after administration of an oxygen 18 labeled compound of the invention and a patient being subjected to a proton beam can be determined by one of ordinary skill in the art, but can be, for example, from about one hour to about 96 hours. Applicants did, for example, a study in which 96 hours was used based on a consideration of the cell cycle time in most human cancer cells in an effort to get at least most of the cancer cells labeled with the oxygen 18 labeled compound (e.g., incorporated into DNA). Thus, a time of exposure to the compound can be chosen to help ensure that incorporation of the heavy nucleoside into DNA occurs over at least one cell cycle in all cells. That is, in one aspect, the "longer the better" may be a principle to adhere to but one of ordinary skill in the art can adjust according to various parameters such as the type of tumor, its aggressiveness, etc. As for the ability to infuse thymidine for a long time, there are clinical studies where massive thymidine infusions (grams/meter squared) have been used safely in cancer patients. However, it is anticipated that such high doses are NOT wise or necessary to achieve radiation sensitization with these heavy molecules. The dose can be "physiologic" based on prior studies and what is known in the art about administration of molecules such as thymidine and their incorporation into DNA. Because the compounds of the invention are not radioactive, there is no safety concern about administration and a radiation dose or effect.

The amount of compound of the invention to be administered to a subject can be determined based on the disclosures provided herein and on other factors. For example, when thymidine is administered in rescue of high dose methotrexate, it is administered as an initial bolus injection of 1.0 g of dThd per sq m, followed by constant infusion of 8 g/sq m/day for 72 hr. In one aspect, thymidine can be administered in high doses such as 75 g/sq m/24 hours.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the formulas of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compound may also be administered intravenously or intraperitoneally by infusion or injection. Solutions of the compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of a formula of the invention, in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple injections or by direct or topical application.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising at least one compound identified in the invention and an instructional material which describes administering the compound or a composition comprising the compound to a cell or a subject. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention. Therefore, the examples should be construed to encompass any and all variations which become evident as a result of the teaching provided herein.

EXAMPLES

The present application discloses compositions and methods to allow for convergence of the increasing availability in clinical radiotherapy of the proton beam, with the emergence of the concept of a "theragnostic agent" in diagnostic radiology and oncology, and with our novel therapeutic use of molecular chemistry applications of substituted Oxygen-18 (a safe, non-radioactive isotope) into critical cellular targets that can be transmutated in vivo by proton bombardment. The predominant literature on $^{18}O$ deals with its precursor role in the production of diagnostic agents like 18F-deoxyglucose for clinical PET scanning that now can be done with mini-cyclotrons in community hospitals. Unexpected results are provided below.

Without wishing to be bound by any particular theory, it is hypothesized herein that an $^{18}O$ targeting agent can be used to target cancer cells and that it will be selectively activated in cancer cells by proton treatment. One of the co-inventors is on the staff of the Hampton University Proton Therapy Institute which houses state of the art proton therapy equipment. The presently described studies were focused on the insertion of a non-radioactive isotope like $^{18}$O into critical cellular targets. Disclosed herein is the preparation and use of heavy thymidine that is incorporated into DNA. Our team has the expertise to make HT possibly in new innovative ways for our particular purpose, plus other nucleosides that we will test in vitro. This endeavor could open a new approach to cancer treatment.

This design science may lead to a clinically feasible treatment entitled "proton activated atomic medicine" to target cancer cells having robust proliferation, a hallmark of the disease in these patients. Some of the new molecules and their use are discussed below.

The application discloses nucleosides, or heavy nucleosides, with O$^{18}$ labels, and optionally also deuterium. For example, presently disclosed modifications of thymidine comprising "heavy" thymidine (HT) are, in one aspect, created by replacing the oxygen atom(s) attached at, for example, the 3' or 5' position of the ribose structure or the oxygen atoms on the Thymine ring structure with non-radioactive oxygen-18 ($^{18}$O) 2-HTd for use in treatment and diagnosis.

Like thymidine, "Heavy-thymidine" is incorporated extensively into the DNA of rapidly proliferating cancer cells because its chemical properties are not altered relative to thymidine as far as incorporation into DNA is concerned. Large doses of thymidine are well tolerated in human cancer patients with concentrations in the serum achieved in the milli-molar range. Subsequent exposure to proton irradiation activates the $^{18}$O by a particle-nuclear reaction that transmutates $^{18}$O into $^{18}$F that results in a break of the new fluorine-phosphorous bond and creates an atomic dipole at the F—C bond on the Thymidine ring. This chemical event destabilizes ribose-phosphate DNA back-bone and base pairing thus produce single- and double strand breaks, clusters lesions that can lead to irreparable DNA damage and enhanced tumor cell killing. This can lead to significant deleterious effects on cancer tissue with few consequences on most normal tissues based on known differences in proliferation indices and the elegant dose distribution created by the proton bragg peak that totally spares "exit dose" to normal tissues. These atomic, chemical, and physical aspects result in the use of lower overall radiation doses and significantly alter acute and late morbidity of radiotherapy. The 2-HTd analogue of thymidine has been made and the former incorporates well into DNA (97%); preliminary investigation with our clinical 230 MeV beam has shown we can activate $^{18}$O with 5 Gye. We now have evidence that there is proton specific radiation sensitization with 2HTd plus a single dose of 8 Gye of protons.

Use of Protons and $^{18}$O Labeled Molecules for Diagnosis and Treatment of Cancer It is disclosed herein that upon exposure to proton irradiation, the particle-nuclear reaction transmutates $^{18}$O into $^{18}$F ((p ($^{18}$O, $^{18}$F), half-life=109.8 minutes).

This new atomic state induced in the incorporated analogues can result in a chemical break of the fluorine-phosphorous bond leading to destabilization of the ribose-phosphate DNA ladder or altered base paring resulting in altered DNA damage repair and increase cellular kill. A simple flow diagram is provided below indicating a type of transmutation disclosed herein:

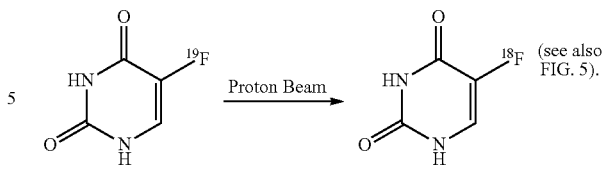

(see also FIG. 5).

It is also disclosed herein that $^{18}$O is converted to $^{18}$F when subjected to a proton beam. Fluorine-18 (18F) is a fluorine radioisotope which is an important source of positrons. It has a mass of 18.0009380(6) u. Because of this short half-life, there is little chance of radiation damage to the patient. It decays by positron emission 97% of the time and electron capture 3% of the time. Both modes of decay yield stable oxygen-18. Fluorine-18 is an important isotope in the radiopharmaceutical industry, and is primarily synthesized into fluorodeoxyglucose (FDG) for use in positron emission tomography (PET scans). It is substituted for hydroxyl and used as a tracer in the scan. Its significance is due to both its short half-life and the emission of positrons when decaying. Until now, dioxaborolane chemistry has been used to label antibodies with radioactive fluorine ($^{18}$F) has been disclosed recently, which allows for positron emission tomography (PET) imaging of cancer. Also, radioactive 2-deoxy-2-[$^{18}$F] fluoro-D-glucose has been used for diagnostic purposes in conjunction with PET. Disclosed herein is its use in labeling DNA, etc. and for better targeting when treating cancer.

Without wishing to be bound by any particular theory, it was hypothesized that targeted radiation sensitization with HTd analogues can be achieved with proton treatment for the following reasons:

High tumor concentration: Daily administration of these analogues can achieve >50% of normal serum concentrations because they are chemically identical to their non-substituted parent, are non-radioactive, and have both been used at pharmacologic doses with little toxicity in humans. We calculate this could easily achieve up to 4.8×10$^8$ heavy atoms per cell, that are assumed to be doubling every ~24 to 48 hours.

Tumor proliferation and up regulated DNA synthetic pathways of cancer cells: The hallmark of cancer is genetic alterations that lead to excessive cellular division. This favors the utilization of HTd analogues and their incorporation into DNA in cancer cells compared to surrounding normal tissues.

Thus, this combination we predict will have a significant deleterious effect on cancer tissues with few consequences on most normal tissues based on cell proliferation kinetics of cancers compared to normal tissues. Furthermore, the elegant dose distribution created by protons that totally spares "exit dose" to normal tissues will contribute to widening the therapeutic window for patients.

Irradiation studies conducted with the proton beam: A clinical 230 MeV beam was used to activate $^{18}$O water placed in the distal end of a spread-out Bragg peak (SOBP) delivering 5 Gye. Our data are consistent with results of $^{18}$O proton activation data with a 160 MeV beam at the M. D. Anderson Cancer Center in Houston. Their data indicate proton activation of $^{18}$O ranging from ~12% in the most distal zone of the Bragg peak, to 100% activation starting at the ~90% percent depth dose. These data confirm the notion that for each nominal energy comprising a SOBP beam, that activation, albeit somewhat inhomogeneous, can occur throughout the irradiated volume. This is supported by the accepted understanding that $^{18}O$ activation peaks at 700 millibarn over the energy range of 8 to 17 MeV, present throughout the SOBP.

A multifunctional laboratory facility was used allowing the irradiation experiments with the proton beam in combination with the HTd analogue to be carried out onsite and we have experience in providing precision dosimetry. We have begun determinations of the enhancement in cell killing with an in vitro colony assay using the glioblastoma cell line U87-MG that has a well characterized genetic background (e.g. P53 mutated or wild-type, functional or deleted PTEN and MGMT methylation status).

A treatment protocol used to test the use of heavy thymidine included 0.125, 0.25, and 0.5 µM exposure for 96 hours. Physiologic serum concentrations in normal and cancer patients the physiologic serum concentration is ~0.3- 1.2 µM. The cells were irradiated with 2 and 8 Gye with 160 MeV protons single fraction and cell death/survival was determined using a colony assay and calculation of survival fraction.

The results of irradiation with 8 Gye single fraction plus 2HTd shows there is increased cytotoxicity compared to the proton beam treatment alone. There was about half a log increased cell kill with 0.5 microgram (a physiologic concentration in humans) of HTd exposed for 96 hours in vitro (FIG. 1). There was no effect on cell survival for the same concentration X time exposure of regular (unsubstituted) Thymidine. These data are proof of principle for the concept of proton activated radiation sensitization.

Figure 2:
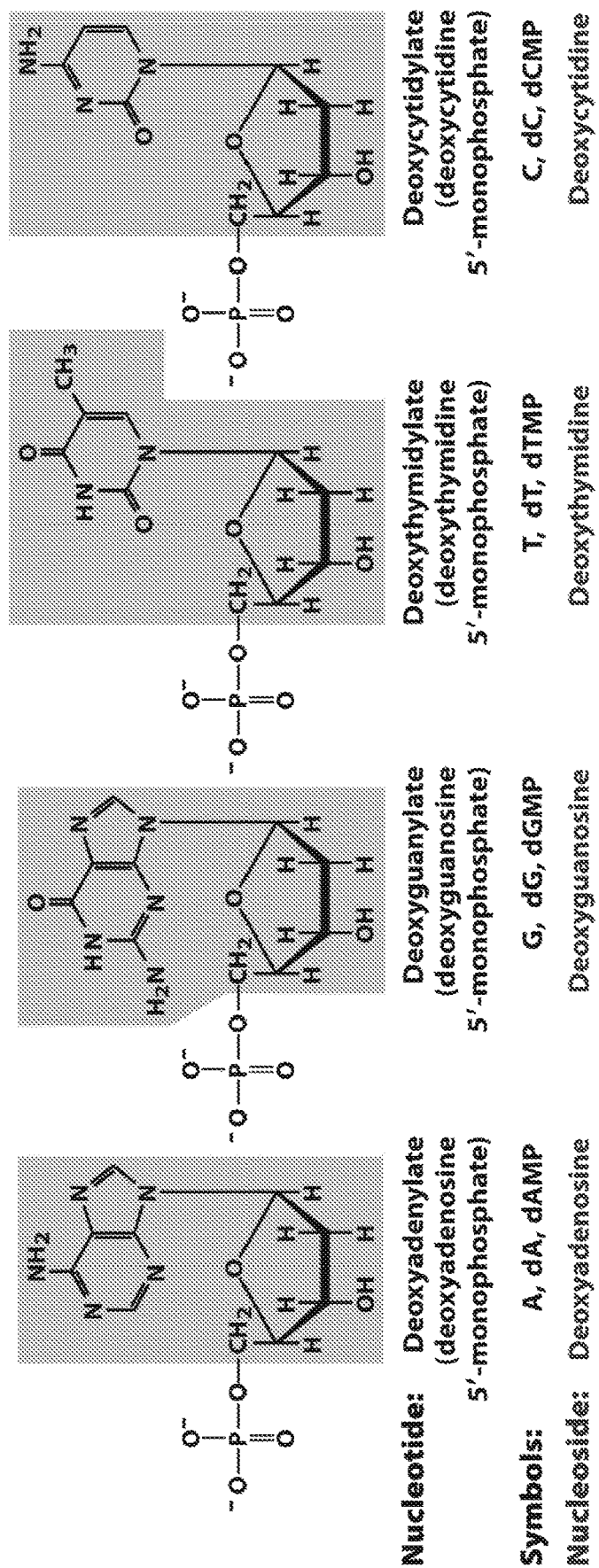
FIG. 2 provides schematically deoxyribonucleotide structures in phosphorylated forms.

Various types of nucleotides can be used and labeled with heavy 180 and other atoms to be subjected to proton activation and transmutation (See FIG. 2 and others described in the next section). A schematic for $^{18}O$ transmutation is provided in FIG. 3 and illustrates some of the chemical consequences once the transmutation occurs. FIG. 4 schematically highlights useful sites available for chemical modification of pyrimidine nucleosides, using 2' deoxyuridine as a model (based on FIG. 6 from Wiebe, Brazilian Archives of Biology and Technology, 2007, 50:3:445-459).

Proton Activation

Proton activated chemical transformation and its biological and other applications. Heavy atom labeled molecules when activated with a proton beam are susceptible for transmutation into a radionuclide which may result in altering chemical bonds and its properties as a molecule. This phenomenon of activating an atom to transmutate to another atom would likely change chemical structure and function. Shown below and in the figures are examples of such possibilities.

Proton Activated Chemical Transformation Examples— The following flow schematic provides three examples:

Example 1.

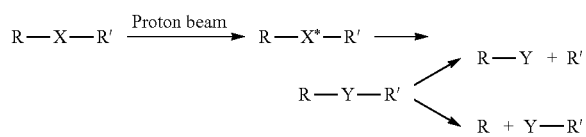

Example 2.

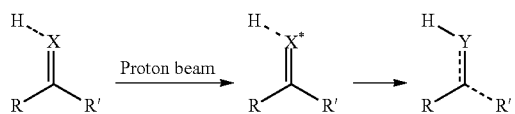

Example 3

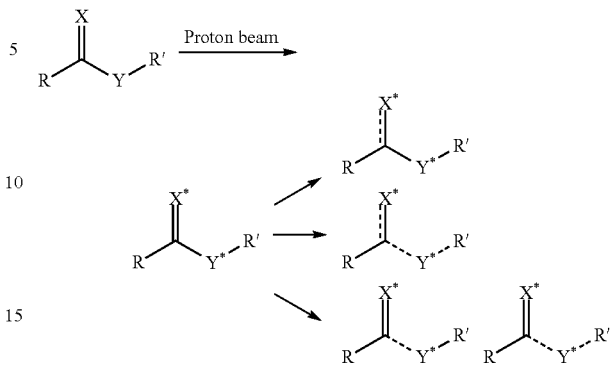

Upon activation and transmutation the transient structural perturbation/fission results in new uses, including therapeutically useful biological application or chemical materials based application such as change in properties of material.

Figure 5A:
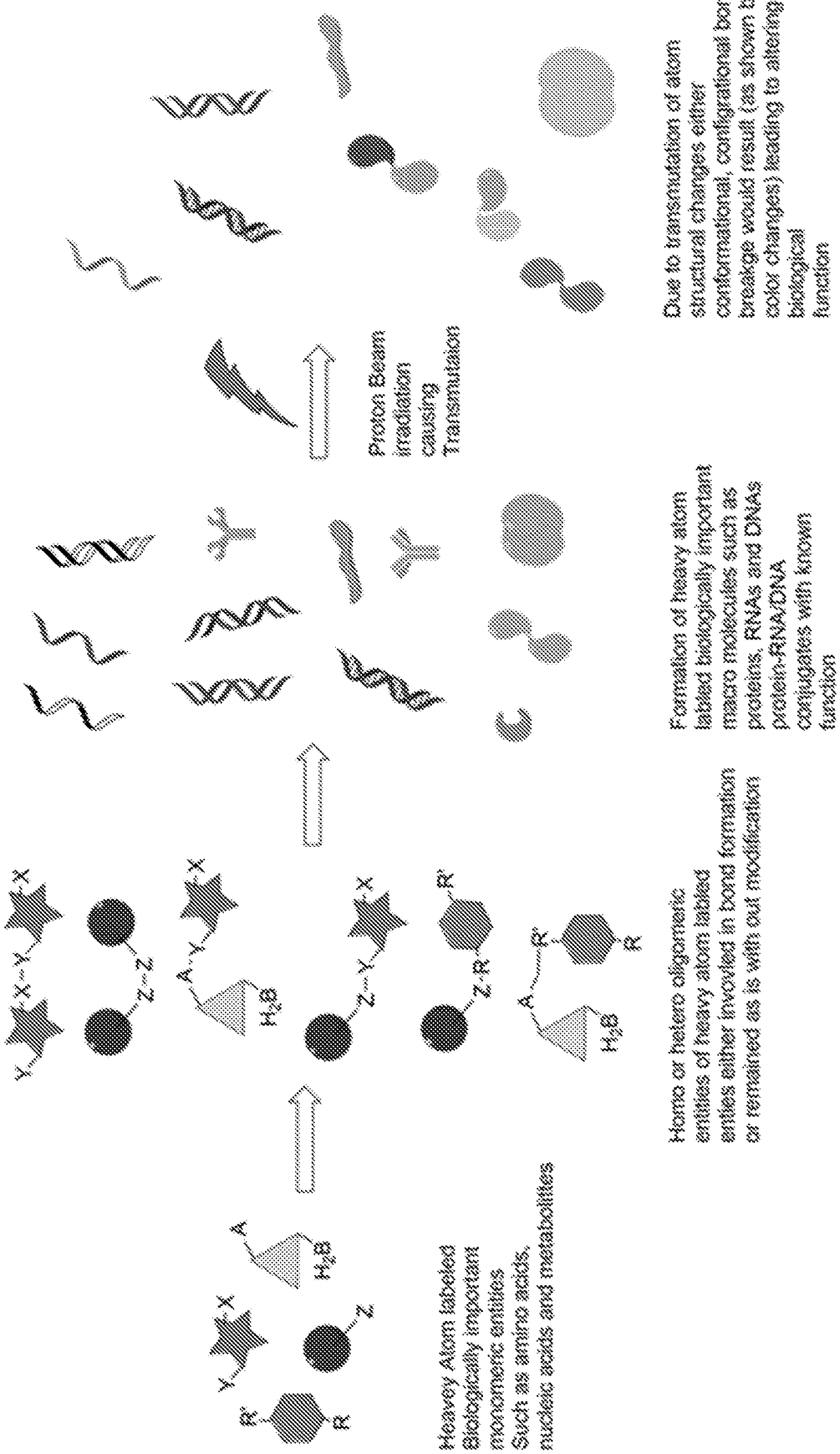
FIG. 5A depicts heavy atom labeled biologically important monomeric entities, transition to oligomeric entities, formation of macromolecules, and the proton beam irradiation causing transmutation and structural changes and leading to altered function.
Figure 5B:
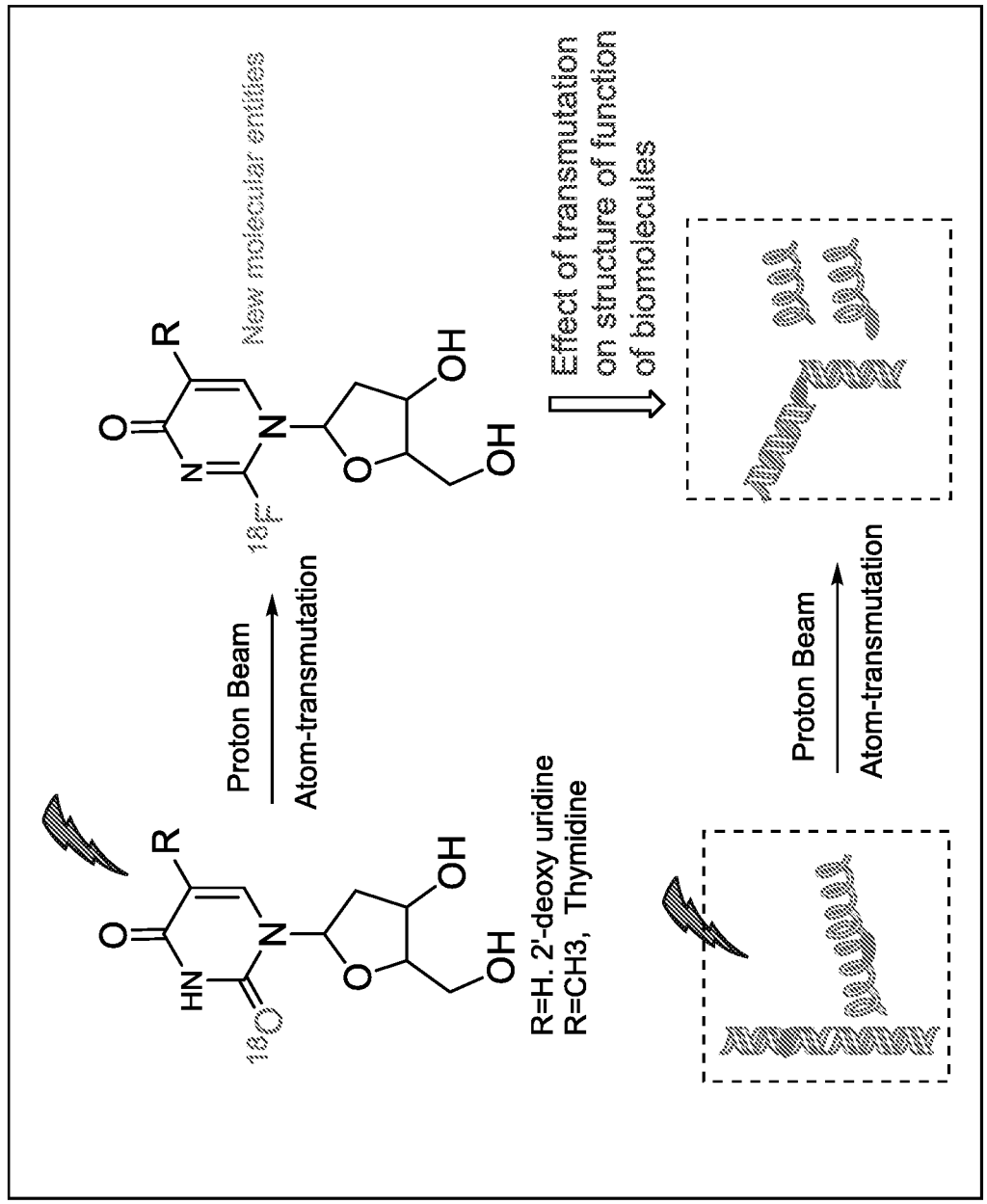
FIG. 5B illustrates molecular details depicting a nucleoside being exposed to a proton beam, atom-transmutation for example from $^{18}$O to $^{18}$F and then altered structure and function of biomolecules.

FIG. 2 provides schematically deoxyribonucleotide structures in phosphorylated forms, while FIG. 3 provides a schematic representation of $^{18}O$ transmutation and the chemical consequences of the transmutation. FIG. 4 further provides a schematic representation of sites for chemical modification of pyrimidine nucleosides and types of modifications that can be made at those sites, using 2' deoxyuridine as a model. FIG. 5, comprising FIGS. 5A and 5B, is a schematic representation of a conceptual depiction of Proton Activated Atomic Medicine. FIG. 5A demonstrates heavy atom labeled biologically important monomeric entities, their transition to oligomeric entities, the formation of macromolecules, and a proton beam causing transmutation and structural changes and leading to altered function. FIG. 5B illustrates molecular details depicting a nucleoside being exposed to a proton beam, atom-transmutation for example from $^{18}O$ to $^{18}F$ and then altered structure and function of biomolecules. (See FIGS. 1-5).

Proton treatment can be coupled with imaging such as immediate PET/CT. The present application encompasses, for example, tumor imaging enhanced by 5-Fluorouracil. Studies have been initiated (data not shown) using fluorine containing compounds (including F containing nanoparticles) in vitro to measure activation with sensitive sodium iodide sensor (see Figures). There is low activity. Cho, et al. (Phys. Med. Biol. 58: 7497, 2013) demonstrates the feasibility of proton-activated implantable markers for proton range verification using PET.

Synthesis and Use of New Molecules for Use in Proton Activated Atomic Medicine

Described below is the synthesis work of various derivatives discussed above.

Use of $^{18}O$-heavy atom labeled biologically active small molecules including natural and synthetic small molecules such as nucleosides, nucleotides, amino acids and their oligomers has been extensively explored for mechanistic and diagnostic purposes for deciphering structure function effects in peptides, proteins, DNAs, RNAs and their fragments.[1-5] This was primarily done for stable isotope mass spectrometry when analyzing the distribution and extents of its presence in cells and tissues. Previous $^{18}O$ labeled compounds were sparsely utilized for other purposes such as diagnostics by imaging.[6-7] There are several methods reported to for synthesis of variety of natural and synthetic analogs of biological small molecules, in particular nucleosides and nucleotides.[8-11]

It is proposed that synthesis of additional $^{18}O$ labeled molecules, which upon proton capture transmutate to another molecule to ensure greater therapeutic efficacy, is encompassed by the present application and the data disclosed herein. Disclosed herein is the first demonstration of the potential therapeutic application of $^{18}O$ labeled nucleotides via protein activation (proton capture) to generate in-situ a new chemical entity ($^{18}O$ labeled compound to $^{18}F$ labeled compound; see FIGS. 5A and 5B), which because of transmutation to another atom permits additional therapeutic efficacy.

Chemistry Procedures:

Preparation of Na$^{18}$OH: In 50 ml plastic vial was measured 5.0 mL of $H_2^{18}O$ (97.4% isotopic enrichment, Isoplex, San Francisco, Calif.) to this was added very slowly and carefully dried powder NaH (230.0 mg, 90% from Aldrich, Cat. #223441) (Caution: This reaction is highly exothermic and vigorous, evolves hydrogen and may cause fire or explosion) over 3-5 minutes with constant stirring in an ice-water bath (5-10° C.). Once the addition is completed, the mixture was further stirred at room temperature for 30 minutes under nitrogen. This solution was used as is for reaction with cyclic anhydride. (Water from the mixture can be lyophilized under vacuo in to get powder to be stored in inert atmosphere).

Synthesis of C2-$^{18}$O-Thymidine: To a solution of 2,5'-cyclic-anhydro thymidine (224.0 mg, 1 mmol, CAS #15425-09-9) was suspended in 1.0 mL of $H_2^{18}O$ and to it was added 0.2 mL of Na$^{18}$OH solution made above. The mixture was stirred at room temperature for over-night (~12 hrs). TLC analysis of reaction mixture indicated complete loss of starting cyclic thymidine and new compound matching the retention time with thymidine was formed. The mixture was then carefully quenched with dil. HCl (0.1 N) till slightly acidic pH~3.0. The reaction mixture was then lyophilized to remove all water to yield off white powder (232.0 mg, 95%). $^1$H-NMR (DMSO-d$_6$): δ 11.3 (s, 1H), 7.69 (s, 1H, ArH), 6.16 (t, J=5 Hz, 1H), 5.21 (d, J=5, 1H), 5.01 (t, J=5, 1H), 4.23 (bs, 1H), 3.76 (brs, 1H), 3.50-3.65 (m, 2H), 2.00-2.12 (m, 2H), 1.71 (s, 3H): Mass spectrometry: observed m/z 244, calcd. m/z 244 for $C_{10}H_{14}N_2O_4{}^{18}O$.

Synthesis of C2-$^{18}$O-3' epi-thymidine: To a solution of 2,3'-cyclic-anhydro thymidine (224.0 mg, 1 mmol, American Advanced Scientific, College Station, Texas; Cat. #AAS-4895. CAS #15981-92-7) was suspended in 1.0 mL of $H_2^{18}O$ and to it was added 0.2 mL of Na$^{18}$OH solution made above. The mixture was stirred at room temperature for over-night (~12 hrs). TLC analysis of reaction mixture indicated complete loss of starting cyclic thymidine and new compound matching the retention time with thymidine was formed. The mixture was then carefully quenched with dil. HCl (0.1 N) till slightly acidic pH~3.0. The reaction mixture was then lyophilized to remove all water to yield off white powder (238.0 mg, 97%). $^1$H-NMR (DMSO-d$_6$): δ 7.70 (1H, ArH), 6.04 (d, J=10 Hz, 1H), 4.24 (bs, 1H), 3.70-3.75 (m, 3H), 3.58 (dd, J=5, 10 Hz, 1H), 2.45-2.54 (m, 3H), 1.82 (d, J=14 Hz, 1H), 1.73 (s, 3H). Mass spectrometry: observed m/z 244, calcd. m/z 244 for $C_{10}H_{14}N_2O_4{}^{18}O$.

Synthesis of C2-$^{18}$O-Uridine: To a solution of 2,5'-cyclic-anhydro uridine (210.0 mg, 1 mmol, CAS #20701-12-6) was suspended in 1.0 mL of $H_2^{18}O$ and to it was added 0.2 mL of Na$^{18}$OH solution made above. The mixture was stirred at room temperature for over-night (~12 hrs). TLC analysis of reaction mixture indicated complete loss of starting cyclic thymidine and new compound matching the retention time with thymidine was formed. The mixture was then carefully quenched with dil. HCl (0.1 N) till slightly acidic pH~3.0. The reaction mixture was then lyophilized to remove all water to yield off white powder (227 mg, 98%). $^1$H-NMR (DMSO-d$_6$): δ 7.70 (1H, ArH), 6.04 (d, J=10 Hz, 1H), 4.24 (bs, 1H), 3.70-3.75 (m, 3H), 3.58 (dd, J=5, 10 Hz, 1H), 2.45-2.54 (m, 3H), 1.82 (d, J=14 Hz, 1H). Mass spectrometry: observed m/z 230, calcd. m/z 230 for $C_9H_{12}N_2O_4{}^{18}O$.

The literature shows that $^{18}O$ incorporates well into HT analogues (97%); evolving methods with this isotope currently includes biomarkers for oncology opening the possibility for the creation of other tagged heavy analogues.

Figure 9:
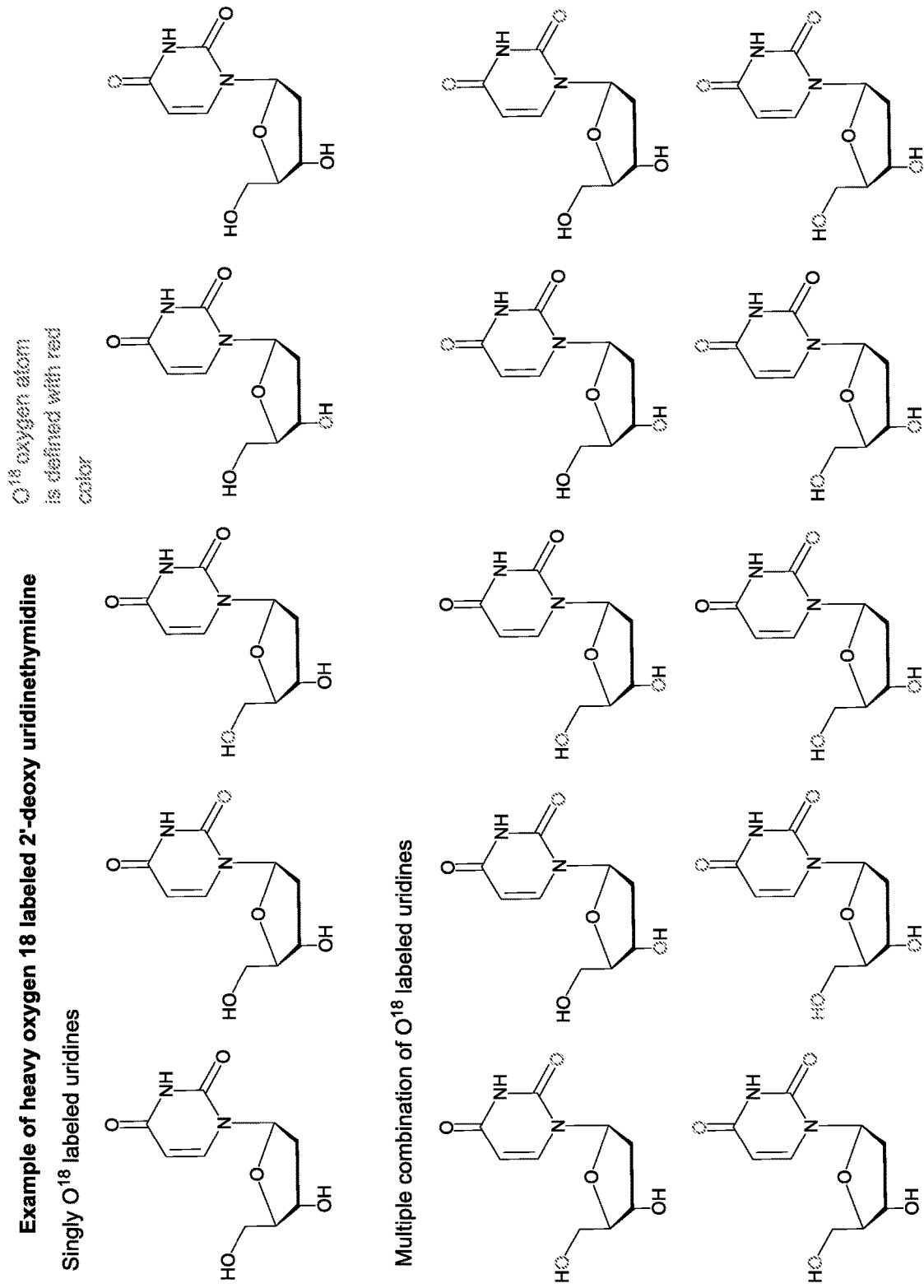
FIG. 9 provides examples of specific heavy oxygen labeled 2'-deoxy uridinethymidines (also referred to as 2'-deoxyuridine) of the invention. Some are singly labeled and others comprise two or more $^{18}$Os. Heavy oxygen 18 is demonstrated in red.

Various heavy oxygen 18 labeled thymidine (a nucleoside) derivatives have been synthesized and are illustrated in the Figures as well as below. See FIG. 6 for synthetic pathways and schemes used to prepare $^{18}O$ labeled compounds. It provides some specific heavy oxygen labeled compounds of the invention. FIG. 7 provides four examples of heavy oxygen 18 labeled thymidine derivatives along with a site for modifications. FIGS. 8-9 provide specific examples of $^{18}O$ labeled compounds of the invention.

Some of the nucleotides that were labeled with heavy oxygen are shown below and in the Figures.

Some singly labeled C2 and C5'-$^{18}$O thymidines of the invention are (See also FIG. 6):

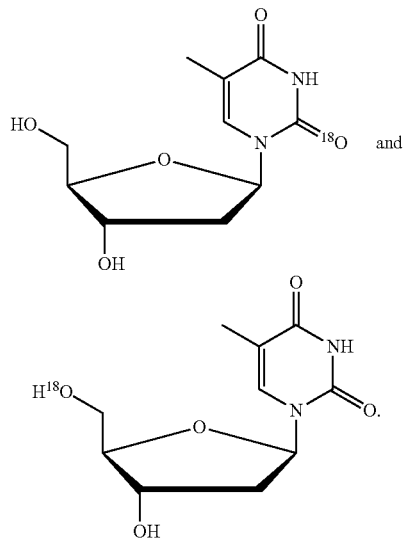

Four sites are also available on deoxyuridine for oxygen substitution. Some singly $^{18}O$ labeled C2 and C5'-$^{18}O$ 2'-deoxyuridines are:

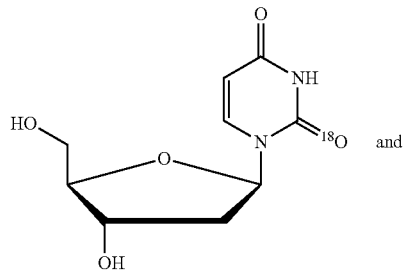

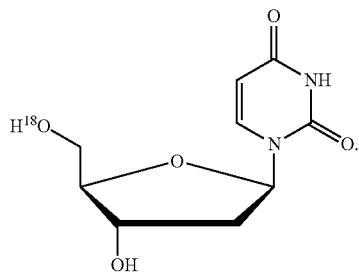
Some useful singly $^{18}$O labeled synthetic thymidine derivatives of the invention labeled with heavy oxygen 18 include, but are not limited to:
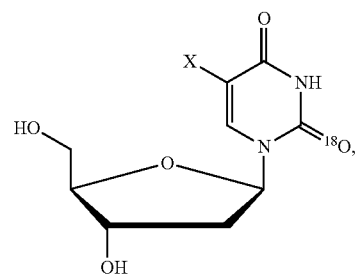
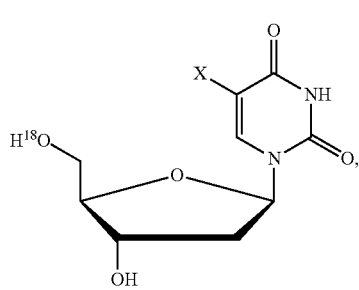
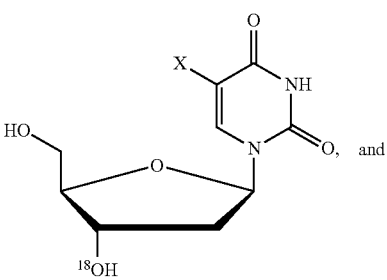
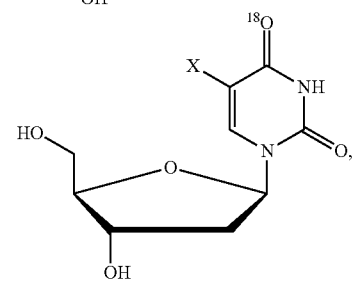
wherein X is a halogen or any other group such as CH$_3$, OH, NH$_2$, OR, N$_3$, CH$_2$X.
Some singly $^{18}$O labeled thymidines of the invention include:
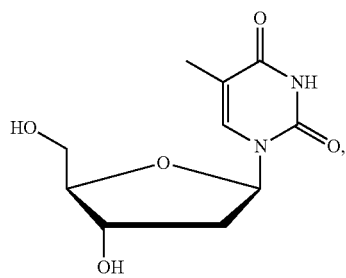
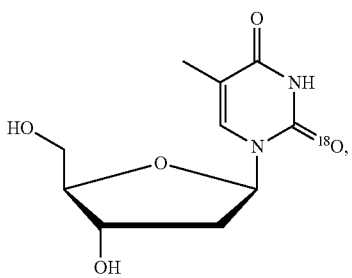
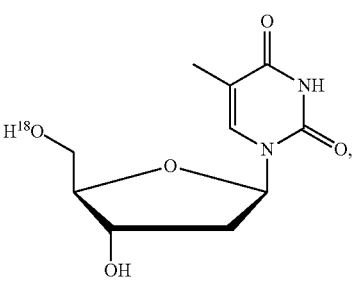
Thymidine
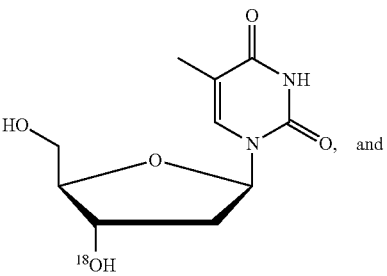
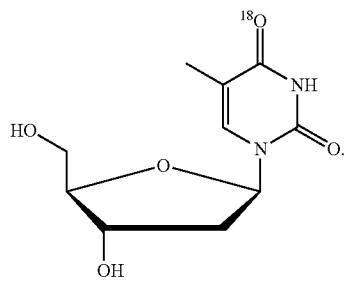

Some multiple $^{18}$O labeled thymidines include:
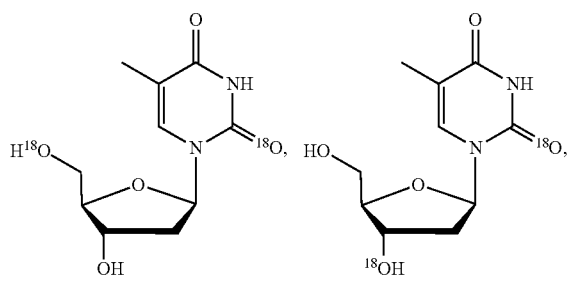
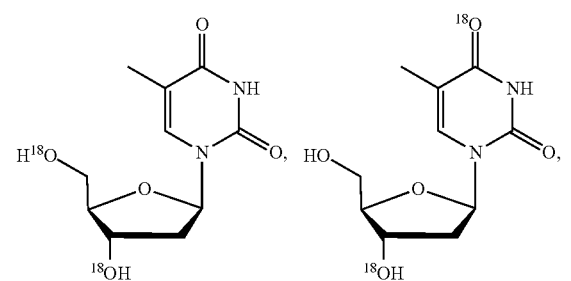
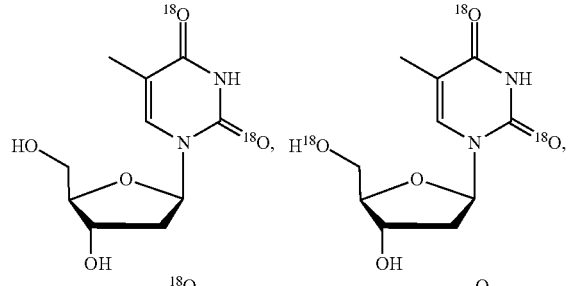
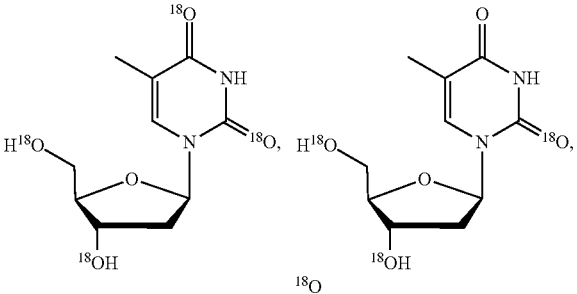
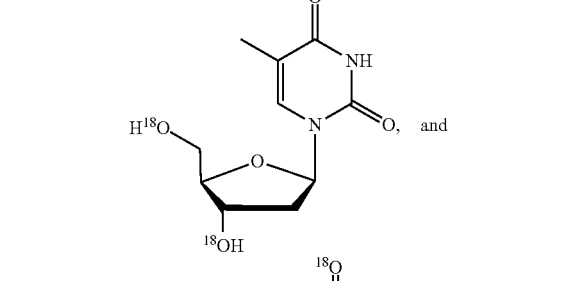
Also provided are examples of heavy oxygen 18 labeled 2'-deoxy uridinethymidine. Singly $^{18}$O labeled uridines, include, but are not limited to:
Some uridines that are multiply labeled with O$^{18}$ include:

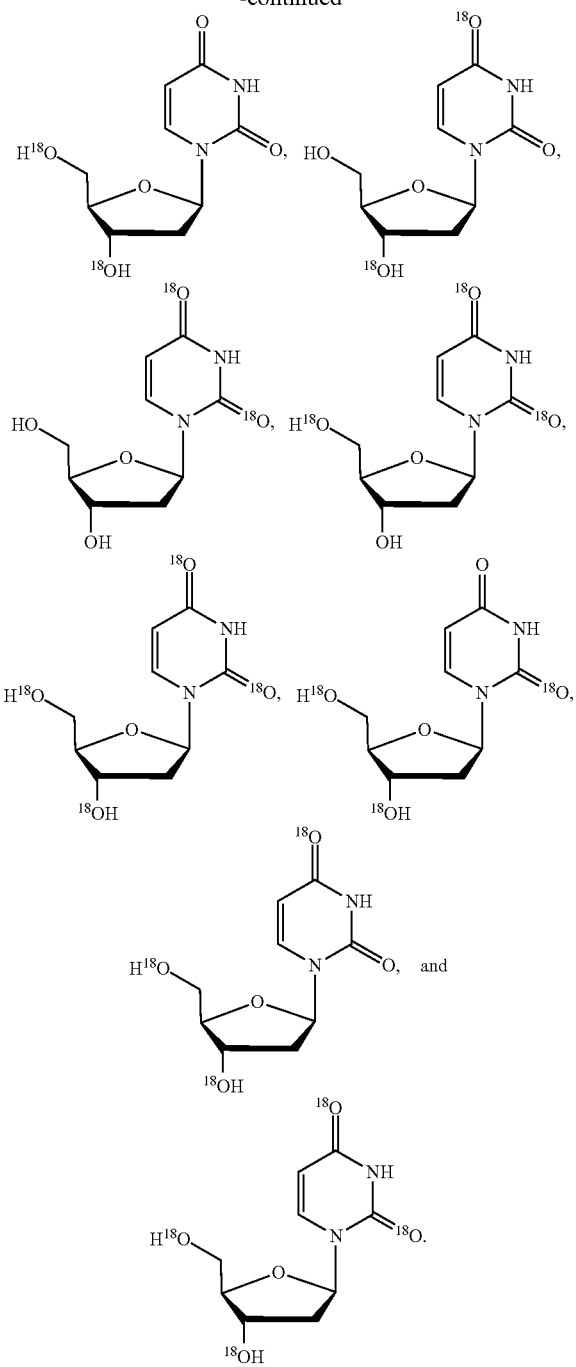

Anhydrous thymidine was combined with $^{18}O$ water (97% pure) to produce the heavy substituted analogue, 2-HTd. The synthesis of this molecule was verified with mass spectrometry (data not shown).

See FIG. 1 for uses of the compounds.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Wang, Meiyao; Shen, Yang; Turko, Illarion V.; Nelson, Daniel C.; Li, Shuwei; 1. Determining Carbapenemase Activity with 18O Labeling and Targeted Mass Spectrometry, Analytical Chemistry (Washington, D.C., United States) (2013), 85(22), 11014-11019.

2. Bergmann, Dominik; Huebner, Florian; Humpf, Hans-Ulrich; Stable Isotope Dilution Analysis of Small Molecules with Carboxylic Acid Functions Using 18O Labeling for HPLC-ESI-MS/MS: Analysis of Fumonisin B 1. Journal of Agricultural and Food Chemistry (2013), 61(33), 7904-7908.

3. Moore, Ronald J.; Schepmoes, Athena A.; Xiao, Wenzhong; Moldawer, Lyle L.; et al; Plasma Proteome Response to Severe Burn Injury Revealed by 18O-Labeled "Universal" Reference-Based Quantitative Proteomics. Journal of Proteome Research (2010), 9(9), 4779-4789.

4. Mori, Masaru; Abe, Kohei; Yamaguchi, Hiroaki; Goto, Junichi; Shimada, Miki; Mano, Nariyasu, Production of 18O-Single Labeled Peptide Fragments during Trypsin Digestion of Proteins for Quantitative Proteomics Using nanoLC-ESI-MS/MS. Journal of Proteome Research (2010), 9(7), 3741-3749.

5. Kolodziejska-Huben, Magdalena; Kaminski, Zbigniew; Paneth, PiotrPreparation of 18O-labeled nicotinamide. Journal of Labelled Compounds & Radiopharmaceuticals (2002), 45(12), 1005-1010.

6. Hamasaki, Tomohiro; Matsumoto, Takahiro; Sakamoto, Naoya; Shimahara, Akiko; Kato, Shiori; Yoshitake, Ayumi; Utsunomiya, Ayumi; Yurimoto, Hisayoshi; Gabazza, Esteban C.; Ohgi, Tadaaki; Synthesis of 18O-labeled RNA for application to kinetic studies and imaging. Nucleic Acids Research (2013), 41(12), e126.

7. Xiao, Bin; Li, You; Zhou, Jianyue; Jiang, Yongyue; Liu, Yan; Qin, Chuanjiang; Method and apparatus for preparation of oxygen 18 labeled water as nuclear medicine diagnostic reagent. Faming Zhuanli Shenqing (2009), CN 101575086 A 20091111.

8. H. Follmann and H. P. C. Hogenkamp, The synthesis of ribose and of adenine nucleotides containing oxygen-18. The Journal of American Chemical Society, 92:3, 1970.

9. Schram, Karl H.; Ratcliff, Steven; Neenan, John; Oxygen-18-labeled nucleosides. 1. A general method for the synthesis of specifically labeled pyrimidine deoxyribosides. Journal of Labelled Compounds and Radiopharmaceuticals (1982), 19(3), 399-404.

10. Solsten, R. Thomas; McCloskey, James A.; Schram, Karl H. Oxygen-18-labeled nucleosides. 2. A general method for the synthesis of specifically labeled pyrimidine ribonucleosides. Nucleosides & Nucleotides (1982), 1(1), 57-64.

11. Schubert, Ernst M.; Schram, Karl H; Oxygen-18-labeled nucleosides. 3. Preparation and mass spectrometric evaluation of 18O2-labeled 1-(β-D-arabinofuranosyl)cytosine and -uracil. Journal of Labelled Compounds and Radiopharmaceuticals (1982), 19(8), 929-35.

12. Wiebe, L., Applications of Nucleoside-based Molecular Probes for the in vivo Assessment of Tumour Biochemistry using Positron Emission Tomography (PET). Brazilian Archives of Biology and Technology (2007), 50:3:445-459.

What is claimed is:

1. A compound of the formula:

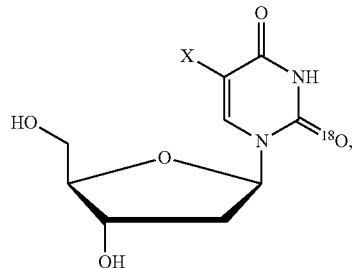

Formula I

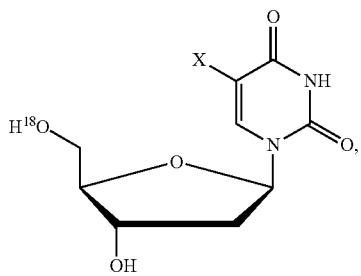

Formula II

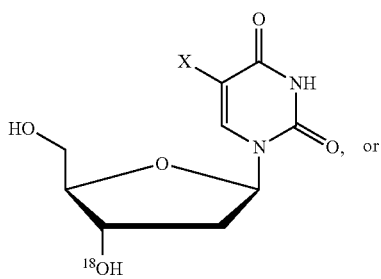

Formula III

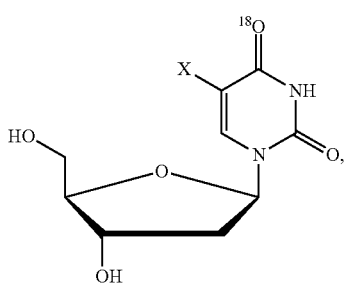

Formula IV wherein:

X is selected from the group consisting of H, CH$_3$, halogen, CF$_3$, OH, NH$_2$, OR, N$_3$, and CH$_2$X;

R is selected from the group consisting of alkyl, alkene, alkyne, and aryl;

wherein three oxygens are $^{18}$O, and said compound optionally comprises at least one additional $^{18}$O.

2. The compound of claim 1, wherein said compound is deuterated.

3. The compound of claim 1, wherein said compound is selected from the group consisting of:

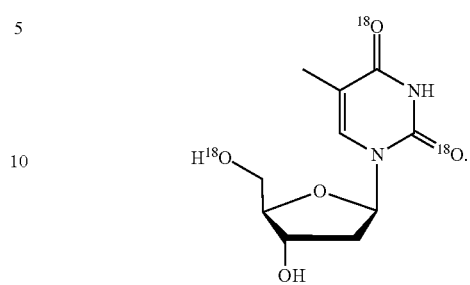

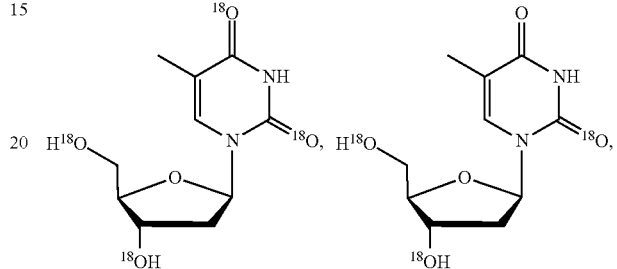

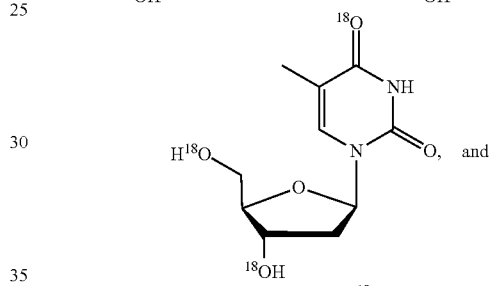

and

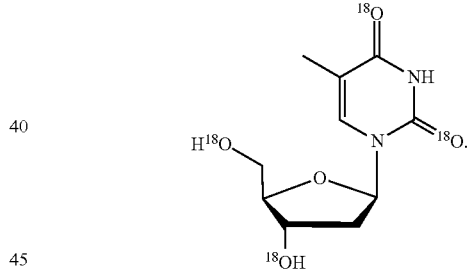

4. A pharmaceutical composition comprising a pharmaceutically-acceptable carrier and a compound of claim 1.

5. A kit comprising an effective amount of at least one compound of claim 1, a pharmaceutically-acceptable carrier, an applicator, and a instructional material for the use thereof.

6. A method of killing a proliferating cancer cell, said method comprising contacting said proliferating cancer cell with an effective amount of a compound of claim 1, allowing said effective amount of said compound to incorporate into the DNA of said proliferating cancer cell, and subjecting said proliferating cancer cell to proton beam therapy.

7. A method of treating a tumor using proton beam therapy in a subject in need thereof, said method comprising administering to said subject a pharmaceutical composition comprising an effective amount of a compound and subjecting said tumor to proton beam therapy, thereby treating a tumor using proton beam therapy, wherein the compound is of the formula:

Formula I
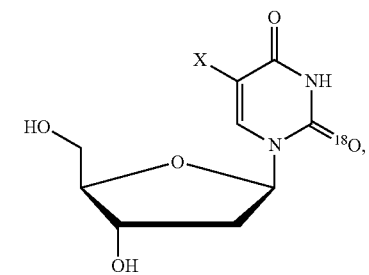
Formula II
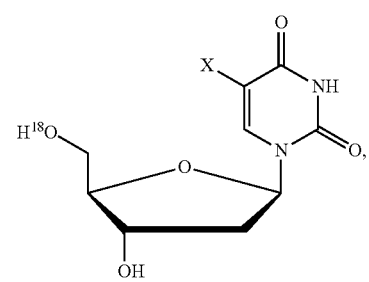
Formula III
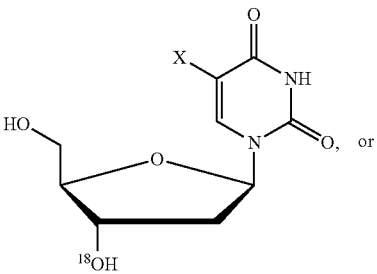
Formula IV
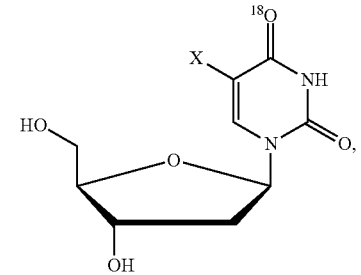
wherein:
X is selected from the group consisting of H, CH$_3$, halogen, CF$_3$, OH, NH$_2$, OR, N$_3$, and CH$_2$X;
R is selected from the group consisting of alkyl, alkene, alkyne, and aryl;
and said compound optionally comprises at least one additional $^{18}$O.
8. The method of claim 7, wherein said compound is selected from the group consisting of:
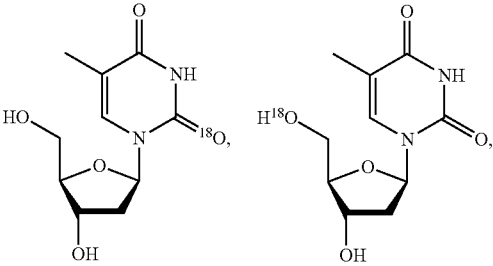
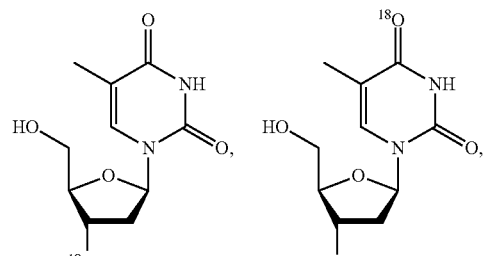
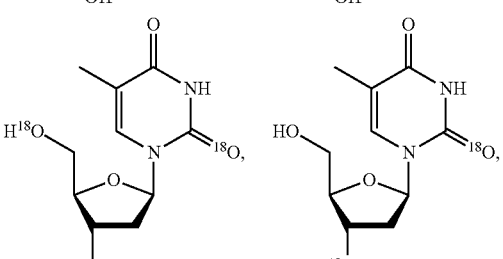
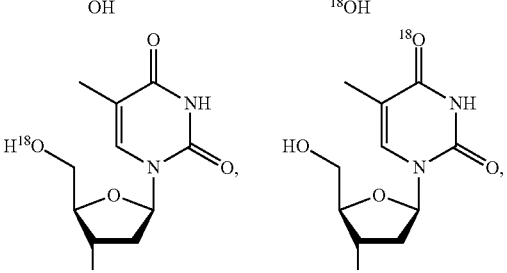
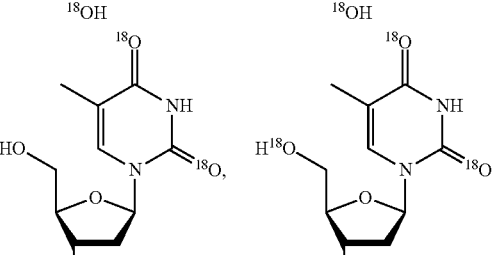
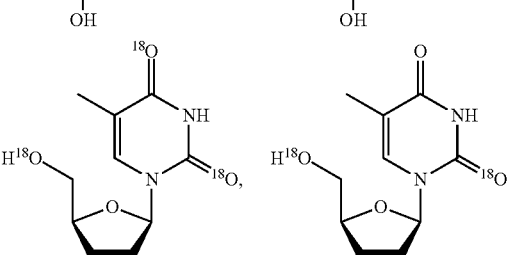

-continued

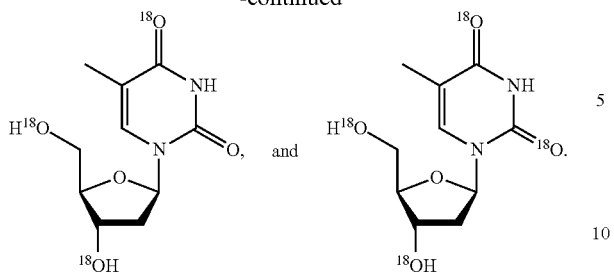

9. The method of claim 7, wherein said compound is deuterated.

10. The method of claim 7, wherein said tumor is imaged using positron emission tomography (PET) or computerized tomography (CT).

11. The method of claim 7, wherein an $^{18}$O of said compound is transmutated to $^{18}$F upon exposure to said proton beam.

12. The method of claim 7, wherein said treatment is used in combination with another treatment selected from conventional x-ray irradiation, chemotherapy, and surgery.

13. The method of claim 7, wherein said proton beam therapy comprises a total dose of about 50 to about 150 Gy.

14. The method of claim 7, wherein said tumor is selected from the group consisting of brain, breast, bone, gastrointestinal tract, prostate, and pediatric tumors.

* * * * *